(12) United States Patent
Nakamura et al.

(10) Patent No.: US 12,344,588 B2
(45) Date of Patent: Jul. 1, 2025

(54) SULFONAMIDE COMPOUNDS AND USE THEREOF

(71) Applicant: Taiho Pharmaceutical Co., Ltd., Tokyo (JP)

(72) Inventors: Hiroyuki Nakamura, Ibaraki (JP); Jing Teng, West Lafayette, IN (US); Nathan Gignac, West Lafayette, IN (US)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 123 days.

(21) Appl. No.: 16/768,031

(22) PCT Filed: Nov. 28, 2018

(86) PCT No.: PCT/IB2018/059430
§ 371 (c)(1),
(2) Date: May 28, 2020

(87) PCT Pub. No.: WO2019/106579
PCT Pub. Date: Jun. 6, 2019

(65) Prior Publication Data
US 2020/0361883 A1     Nov. 19, 2020

Related U.S. Application Data

(60) Provisional application No. 62/592,023, filed on Nov. 29, 2017.

(51) Int. Cl.
C07D 271/113 (2006.01)
A61K 9/00 (2006.01)

(52) U.S. Cl.
CPC ........ C07D 271/113 (2013.01); *A61K 9/0053* (2013.01); *C07B 2200/13* (2013.01)

(58) Field of Classification Search
CPC .............. C07D 271/113; A61K 9/0053; C07B 2200/13
See application file for complete search history.

(56) References Cited

U.S. PATENT DOCUMENTS

| | | | |
|---|---|---|---|
| 8,022,225 | B2 | 9/2011 | Ono et al. |
| 10,889,555 | B2 | 1/2021 | Miyahara et al. |
| 2006/0110383 | A1 | 5/2006 | Honjo et al. |
| 2009/0118222 | A1 | 5/2009 | Nomura et al. |
| 2010/0041655 | A1 | 2/2010 | Ono et al. |
| 2011/0218248 | A1 | 9/2011 | Jordine et al. |
| 2013/0005678 | A1 | 1/2013 | Sandvold et al. |
| 2019/0010158 | A1 | 1/2019 | Ishida |
| 2019/0350932 | A1 | 11/2019 | Miura et al. |
| 2020/0157066 | A1* | 5/2020 | Hara ........... A61P 35/00 |
| 2020/0361883 | A1 | 11/2020 | Nakamura et al. |
| 2020/0399235 | A1 | 12/2020 | Miyahara et al. |
| 2020/0405697 | A1 | 12/2020 | Ueno et al. |

FOREIGN PATENT DOCUMENTS

| | | |
|---|---|---|
| AU | 2015203322 A1 | 7/2015 |
| EP | 3099717 A1 | 12/2016 |
| EP | 3466934 A1 | 4/2019 |
| RU | 2543621 C2 | 3/2015 |
| RU | 2718914 C2 | 4/2020 |
| WO | 99/21859 A1 | 5/1999 |
| WO | 00/029375 A1 | 5/2000 |
| WO | 01/10454 A2 | 2/2001 |
| WO | 01/83450 A2 | 11/2001 |
| WO | 02/018390 A1 | 3/2002 |
| WO | 2004/004771 A1 | 1/2004 |
| WO | 2004/014300 A2 | 2/2004 |
| WO | 2006/080509 A1 | 8/2006 |
| WO | 2007/083089 A1 | 7/2007 |
| WO | 2007/089018 A1 | 8/2007 |
| WO | 2009/023059 A2 | 2/2009 |
| WO | 2015/117002 A1 | 8/2015 |
| WO | 2015/138920 A1 | 9/2015 |
| WO | 2016/040880 A1 | 3/2016 |
| WO | 2016/075309 A1 | 5/2016 |
| WO | 2017/111074 A1 | 6/2017 |
| WO | 2017/150725 A1 | 9/2017 |
| WO | WO-2017209155 A1 * | 12/2017 ......... A61K 31/4245 |
| WO | 2019/210332 A2 | 10/2019 |

OTHER PUBLICATIONS

Vippagunta et al. (Advanced Drug Delivery Reviews: 2001; 48, 3-26). (Year: 2001).*
International Search Report issued in related International Patent Application No. PCT/JP2017/020166 dated Jul. 25, 2017.
Syed et al., "Synthesis, QSAR and anti-HIV activity of new 5-benzylthio-1,3,4-oxadiazoles derived from alpha-amino acids," Journal of Enzyme Inhibition and Medicinal Chemistry, 26: 668-680 (2011).
Zareef et al., "Carbonic anhydrase inhibitors. Inhibition of human tumor-associated isozymes IX and cytosolic isozymes I and II with some 1,3,4-oxadiazole-thiols," Journal of Enzyme Inhibition and Medicinal Chemistry, 21: 351-359 (2006).
Jordan et al., "Ribonucleotide Reductases," Annual Review of Biochemistry, 67: 71-98 (1998).
Elford et al., "Ribonucleotide Reductase and Cell Proliferation," The Journal of Biological Chemistry, 245: 5228-5233 (1970).
Nilsson et al., "Metabolic enzyme expression highlights a key role for MTHFD2 and the mitochondrial folate pathway in cancer," Nature Communications, 5: 3128 (2014).
Liu et al., "Ribonucleotide reductase small subunit M2 serves as a prognostic biomarker and predicts poor survival of colorectal cancers," Clinical Science, 124: 567-578 (2013).

(Continued)

Primary Examiner — Clinton A Brooks
Assistant Examiner — Jerica Katlynn Wilson
(74) Attorney, Agent, or Firm — Morgan, Lewis & Bockius LLP

(57) ABSTRACT

The present disclosure relates to novel crystalline forms of sulfonamide compounds, pharmaceutical compositions containing the crystalline form compounds and methods of preparing and using the same.

27 Claims, 10 Drawing Sheets

(56) References Cited

OTHER PUBLICATIONS

Shao et al., "Targeting ribonucleotide reductase for cancer therapy," Expert Opinion on Therapeutic Targets, 17: 1423-1437 (2013).
Finch et al., "Triapine (3-Aminopyridine-2-carboxaldehyde-thiosemicarbazone): A Potent Inhibitor of Ribonucleotide Reductase Activity with Broad Spectrum Antitumor Activity," Biochemical Pharmacology, 59: 983-991 (2000).
Zhu et al., "Inhibitory mechanisms of heterocyclic carboxaldehyde thiosemicabazones for two forms of human ribonucleotide reductase," Biochemical Pharmacology, 78: 1178-1185 (2009).
Yen et al., "Characterization of a Hydroxyurea-resistant Human KB Cell Line with Supersensitivity to 6-Thioguanine," Cancer Research, 54: 3686-3691 (1994).
Kalinowski et al., "The Evolution of Iron Chelators for the Treatment of Iron Overload Disease and Cancer," Pharmacological Reviews, 57: 547-583 (2005).
Kunos et al., "Management of 3-aminopyridine-2-carboxaldehyde thiosemicarbazone-induced methemoglobinemia," Future Oncology, 8: 145-150 (2012).
Office Action issued in related Indian Patent Application No. 201817049173 dated Sep. 25, 2019.
Syed et al., STN International HCAPLUS database (Columbus, Ohio) Accession No. 2011: 1168579.
Cowen et al., STN International HCAPLUS database (Columbus, Ohio) Accession No. 2007: 816399.
Pardoll et al., "The blockade of immune checkpoints in cancer immunotherapy," Nature Reviews Cancer, 12 (4): 252-264 (2016).
Topalian et al., "Safety, Activity, and Immune Correlates of Anti-PD-1 Antibody in Cancer," The New England Journal of Medicine, 366 (26): 2443-2454 (2012).
International Search Report issued in related International Patent Application No. PCT/JP2018/043697 dated Feb. 5, 2019.
Sigmond et al., "The synergistic interaction of gemcitabine and cytosine arabinoside with the ribonucleotide reductase inhibitor triapine is schedule dependent," Biochemical Pharmacology, 73, 1548-1557 (2007).
28 Leukemia Chemistry Regimen, Internetarchive waybackmachine https://www.saiseikai-hp.chuo.fukuoka.jp/cancer/pdf/rejimen/28.pdf (retrieved Nov. 12, 2021).
International Search Report issued in related International Patent Application No. PCT/JP2020/021108 dated Jul. 14, 2020.
Kuznetsova, "Qualitative X-ray analysis: Guidelines," Federal Agency for Education State Educational Institution of Higher Professional Education, Irkutsk State University, Department of General Physics (2005).
Small Medical Encyclopedia, Moscow, Medicine, 5: 90-96 (1996).
Office Action issued in related Russian Patent Application No. 2020121153 dated Feb. 11, 2022.
Yuchi Kato "Regimen Management in cancer pharmacotherapy," Japanese Journal of Drug Informatics, 11 (4): 217-222 (2010).
28 Leukemia Chemistry Regimen, Internetarchive waybackmachine https://www.saiseikai-hp.chuo.fukuoka.jp/cancer/pdf/rejimen/25.pdf (retrieved Nov. 12, 2021).
Murren et al., "Phase I and Pharmacokinetic Study of Triapine, a Potent Ribonucleotide Reductase Inhibitor, Administered Daily for Five Days in Patients with Advanced Solid Tumors," Clinical Cancer Research, 9: 4092-4100 (2003).
Goss et al., "Gene expression signature based screening identifies ribonucleotide reductase as a candidate therapeutic target in Ewing sarcoma," Oncotarget, 7 (39): 63003-63019 (2016).
International Search Report issued in corresponding International Patent Application No. PCT/JP2021/033854 dated Nov. 30, 2021.
International Search Report issued in corresponding International Patent Application No. PCT/JP2021/033855 dated Nov. 30, 2021.
Kharkevich D.A., Pharmacology/Textbook, 2010, 10th edition, pp. 76-77.
Office Action dated Dec. 19, 2023, issued in related Russian Patent Application No. 2021139254.
Database Embase [Online] Elsevier Science Publishers, Amsterdam, NL; (Dec. 1, 2019), Hoshino T et al: "TAS1553, a novel class of RNR inhibitor, demonstrates synergistic antitumor efficacy in combination with nucleoside analogues", XP002811658, Database accession No. EMB-638177593.
Extended European Search Report dated Jun. 18, 2024, issued in related European Patent Application No. 21869378.6.
Office Action issued in related Chinese Patent Application No. 201780045742.8 dated Aug. 26, 2021 (see partial English translation).
Faqing et al., "Medicinal Chemistry," 67 (2012) (see CN OA translation).
Aye et al., "Ribonucleotide reductase and cancer: biological mechanisms and targeted therapies," Oncogene, 34: 2011-2021 (2015).
Reynolds et al., "A View on Drug Development for Cancer Prevention," Cancer Discovery, 13(5): 1058-1083 (2023).
Office Action dated May 8, 2024, issued in related U.S. Appl. No. 16/767,306.
International Search Report issued in corresponding International Patent Application No. PCT/IB2018/059430 dated Feb. 5, 2019.
Ahmad et al, "Identification of Non-nucleoside Human Ribonucleotide Reductase Modulators," Journal of Medicinal Chemistry, 58 (24): 9498-9509 (2015).
Extended European Search Report dated May 30, 2023 issued in European Patent Application No. 20814485.7.
A. Passardi, et al., "Immune Checkpoints as a Target for Colorectal Cancer Treatment," International Journal of Molecular Sciences, vol. 18, No. 6, Jun. 21, 2017.
Office Action issued in related Russian Patent Application No. 2021139254 dated Sep. 21, 2022.
Belikov, Pharmaceutical Chemistry, Moscow, "MEDpress-inform," 27-29 (2007).
Dyson, Chemistry of Synthetic Drugs, "MIR" Moscow (1964).
Celgene Corporation, "A phase 3, randomized, double-blind, placebo-controlled study to compare efficacy and safety of oral azacitidine plus best supportive care versus best supportive care as maintenance therapy in subjects with acute myeloid leukemia in complete remission," Protocol CC-486-AML-001, <<https://cdn.clinicaltrials.gov/large-docs/35/NCT01757535/Prot_000.pdf>> (2018).
Döhner et al., "Diagnosis and management of acute myeloid leukemia in adults: recommendations from an international expert panel, on behalf of the European LeukemiaNet," Blood, 115(3): 453-474 (2010).
Office Action dated Nov. 15, 2024, issued in Russian Patent Application No. 2023109542.
Takahashi et al., "SLFN11 is a sensitivity biomarker for TAS1553 a clinical ribonucleotide reductase inhibitor" [Poster] SLFN Symposium, May 9, 2023.
Hoshino et al., "TAS1553, a novel class of RNR inhibitor, demonstrates synergistic antitumor efficacy in combination with nucleoside analogues" [Poster: P3-04] The 27th Annual Meeting of Japanese Assosiation for Molecular Target Therapy of Cancer, Jun. 22, 2023 (attached program with machine translation).
Fukushima et al., "Schlafen 11 (SLFN11) as a predictive biomarker of the response to TAS1553, a novel small molecule ribonucleotide reductase subunit interaction inhibitor" [Poster:P3-03] The 27th Annual Meeting of Japanese Assosiation for Molecular Target Therapy of Cancer, Jun. 22, 2023 (attached program with machine translation).
Ueno et al., "TAS1553, a small molecule subunit interaction inhibitor of ribonucleotide reductase, exhibits antitumor activity by causing DNA replication stress" Communications Biology, vol. 5, Article No. 571 (2022).
Fukushima et al., "Schlafen11 (SLFN11) as a predictive biomarker of the response to TAS1553, a novel small molecule ribonucleotide reductase subunit interaction inhibitor" [Abstract P020] EORTC-NCI-AACR 2021, Oct. 7, 2021.
Fukushima et al., "Schlafen11 (SLFN11) as a predictive biomarker of the response to TAS1553, a novel small molecule ribonucleotide reductase subunit interaction inhibitor" [Slides] EORTC-NCI-AACR 2021, Oct. 7, 2021.
Anonymous, "Phase 1 Clinical Study of TAS1440 and TAS1553" [Slides] 62nd ASH annual meeting, Dec. 5, 2020.

(56) References Cited

OTHER PUBLICATIONS

Fukushima et al., "TAS1553, a novel class of RNR inhibitor, has robust antitumor activity in murine syngeneic tumor models as a single agent and in combination with anti-PD-1 checkpoint inhibitor" [Poster:202] AACR-NCI-EORTC annual symposium, Oct. 24, 2020.

Fukushima et al., "TAS1553, a novel protein-protein interaction inhibitor against RNR, demonstrates antitumor activity via the inhibition of de novo deoxyribonucleotides biosynthesis" [Slides] Annual Meeting of Japanese Association for Molecular Target Therapy of Cancer, Oct. 6, 2020 (attached program with machine translation).

Hoshino et al., "TAS1553, a novel protein-protein interaction inhibitor against RNR, demonstrates antitumor activity via the induction of dATP pool reduction and DNA replication stress" [Poster] The 24th JFCR-ISCC symposium, Dec. 11, 2019 (attached program).

Hoshino et al., "TAS1553, a novel protein-protein interaction inhibitor against RNR, demonstrates antitumor activity via the induction of dATP pool reduction and DNA replication stress" [Slides] The 24th JFCR-ISCC symposium, Dec. 11, 2019.

Ueno et al., "Discovery of a novel RNR inhibitor inhibiting protein binding, TAS1553" [Slides] Tsuruoka Conference on Nucleic Acid Metabolism, Aug. 31, 2019.

Ueno et al., "Discovery of a novel RNR inhibitor inhibiting protein binding, TAS1553" [Slides] Tsuruoka Conference on Nucleic Acid Metabolism, Aug. 31, 2019 (with machine translation).

Hoshino et al., "TAS1553, a novel class of RNR inhibitor, demonstrates synergistic antitumor efficacy in combination with nucleoside analogues" [Poster:A063] EORTC-NCI-AACR 2019, Oct. 26, 2019.

Hoshino et al., "TAS1553, a novel protein-protein interaction inhibitor against RNR, causes the inhibition of tumor cell proliferation via the induction of dATP pool reduction and DNA replication stress" [Poster] EORTC-NCI-AACR 2018, Nov. 13, 2018.

Ueno et al., "TAS1553, a novel class of RNR inhibitor, demonstrates antitumor activity in preclinical models" [Poster: PB-021] EORTC-NCI-AACR 2018, Nov. 13, 2018.

Ueno et al., "TAS1553, a novel class of RNR inhibitor, demonstrates antitumor activity in preclinical models" [Abstract: PB-021] e62-63 EORTC-NCI-AACR 2018, Nov. 13, 2018.

Hoshino et al., "TAS1553, a novel class of RNR inhibitor, demonstrates synergistic antitumor efficacy in combination with nucleoside analogues" [Abstract:A063] EORTC-NCI-AACR 2019, Oct. 26, 2019.

Office Action dated Feb. 7, 2025, issued in related U.S. Appl. No. 16/767,306.

Zeidner, et al., "A phase II trial of sequential robonucleotide reductase inhibition in aggressive myeloproliferative neoplasms", Haematologica 2014;99(4):672-678; https://doi.org/10.3324/haematol.2013.097246.

Office Action dated Feb. 6, 2025, issued in related Russian Patent Application No. 2023109543.

Chao et al., "A phase I and pharmacokinetic study of oral 3-aminopyridine-2-carboxaldehyde thiosemicarbazone (3-AP, NSC #663249) in the treatment of advanced stage solid cancers—A California Cancer Consortium Study", Cancer Chemother Pharmacol., vol. 69, No. 3, Mar. 2012, pp. 1-15.

Nelen et al., "Targeting replication stress in neuroblastoma by exploiting the synergistic potential of second generation RRM2 and CHK1 inhibitors", bioRxiv, Mar. 2, 2025, 48 pages.

Office Action issued in Taiwanese Patent Application No. 110134368, dated Feb. 27, 2025.

\* cited by examiner

[Figure 1]
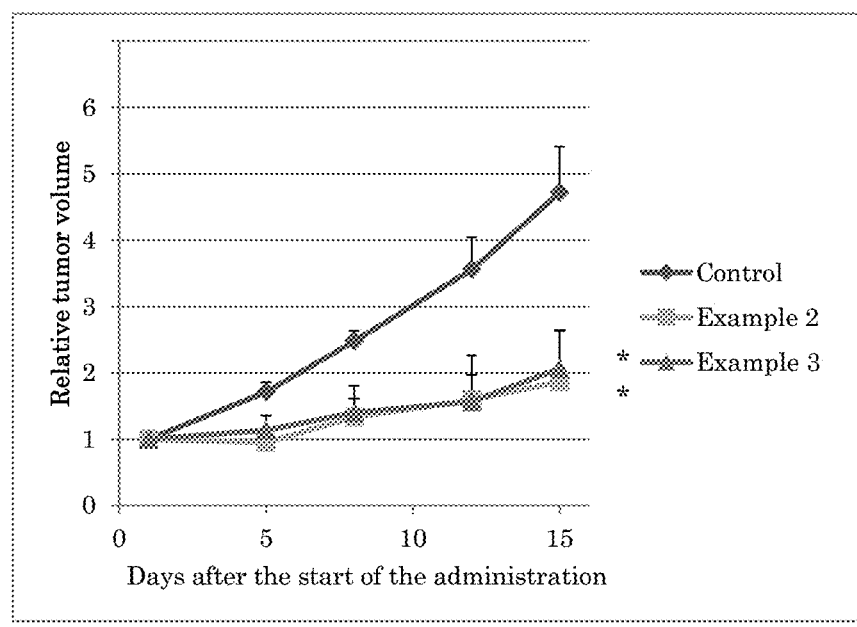
[Figure 2]
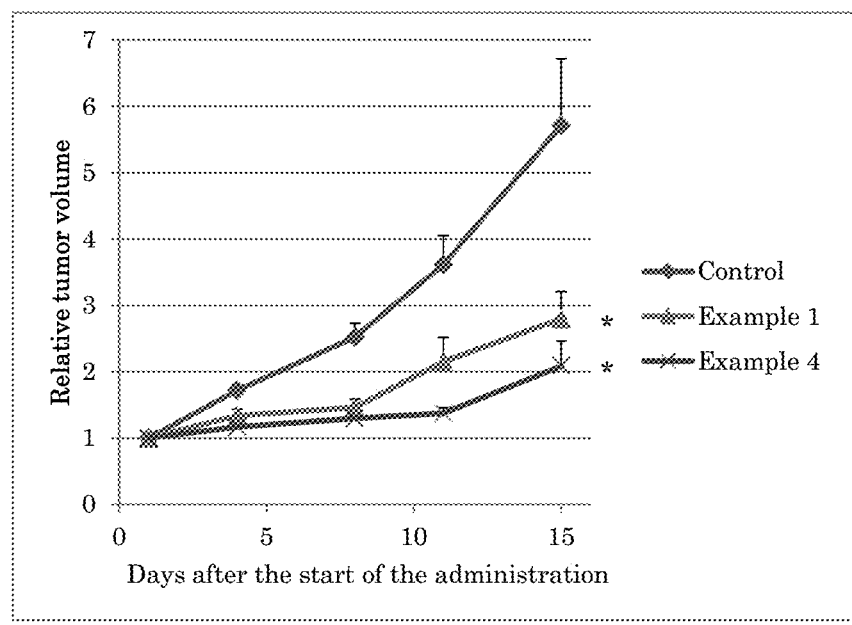

[Figure 3]
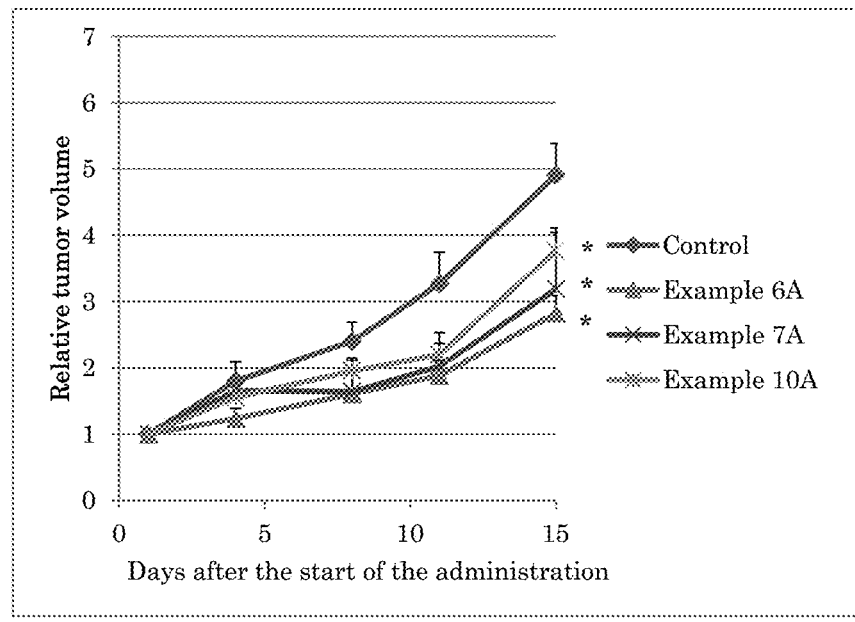
[Figure 4]
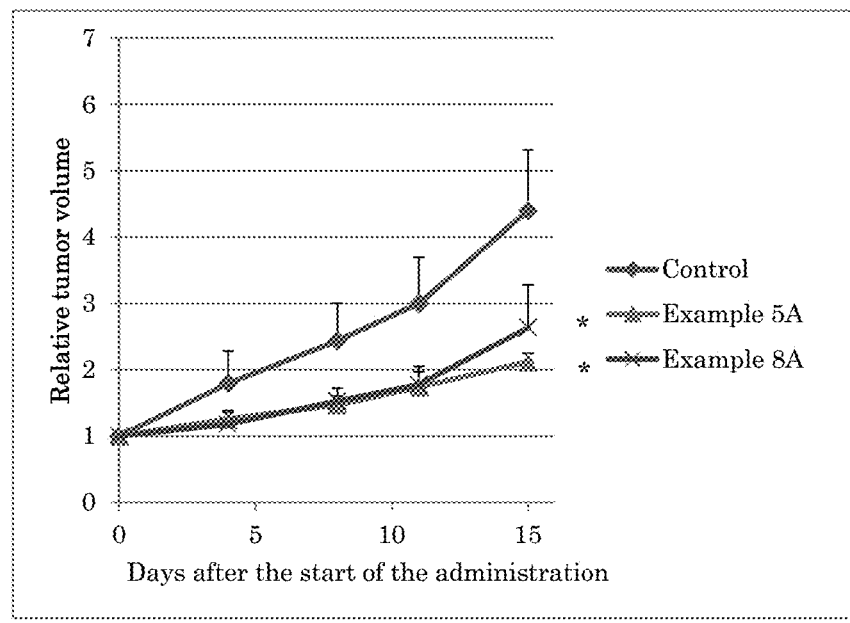

[Figure 5]
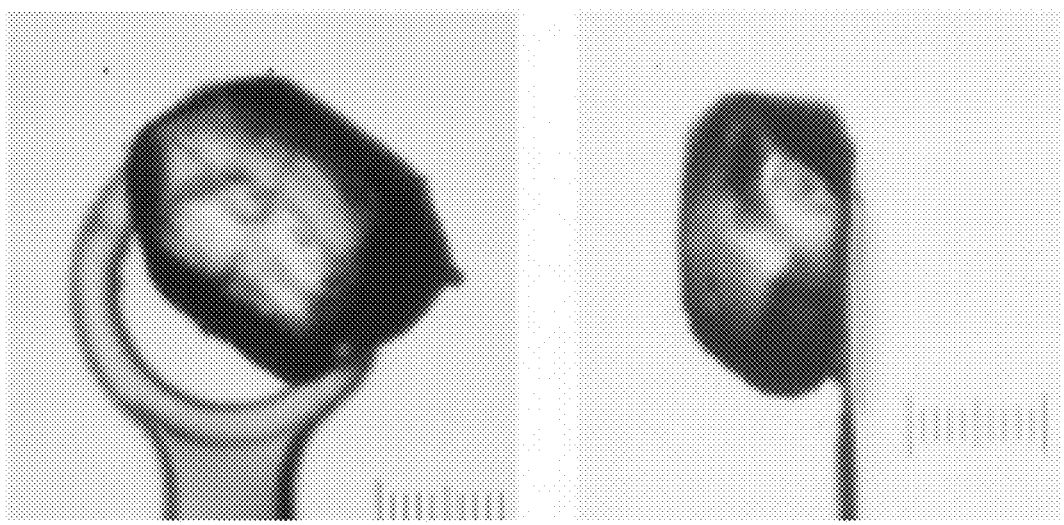

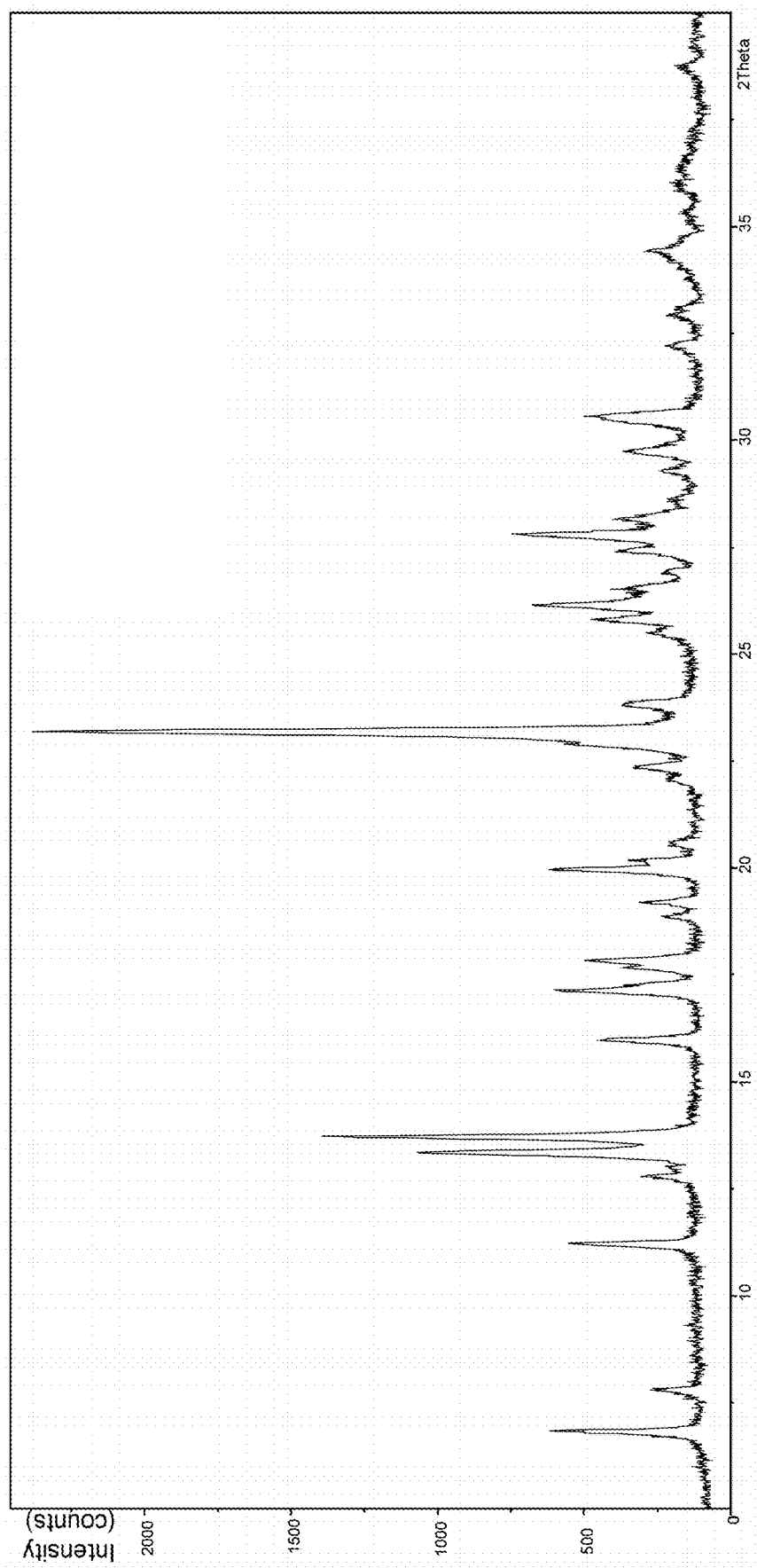

[Figure 7]
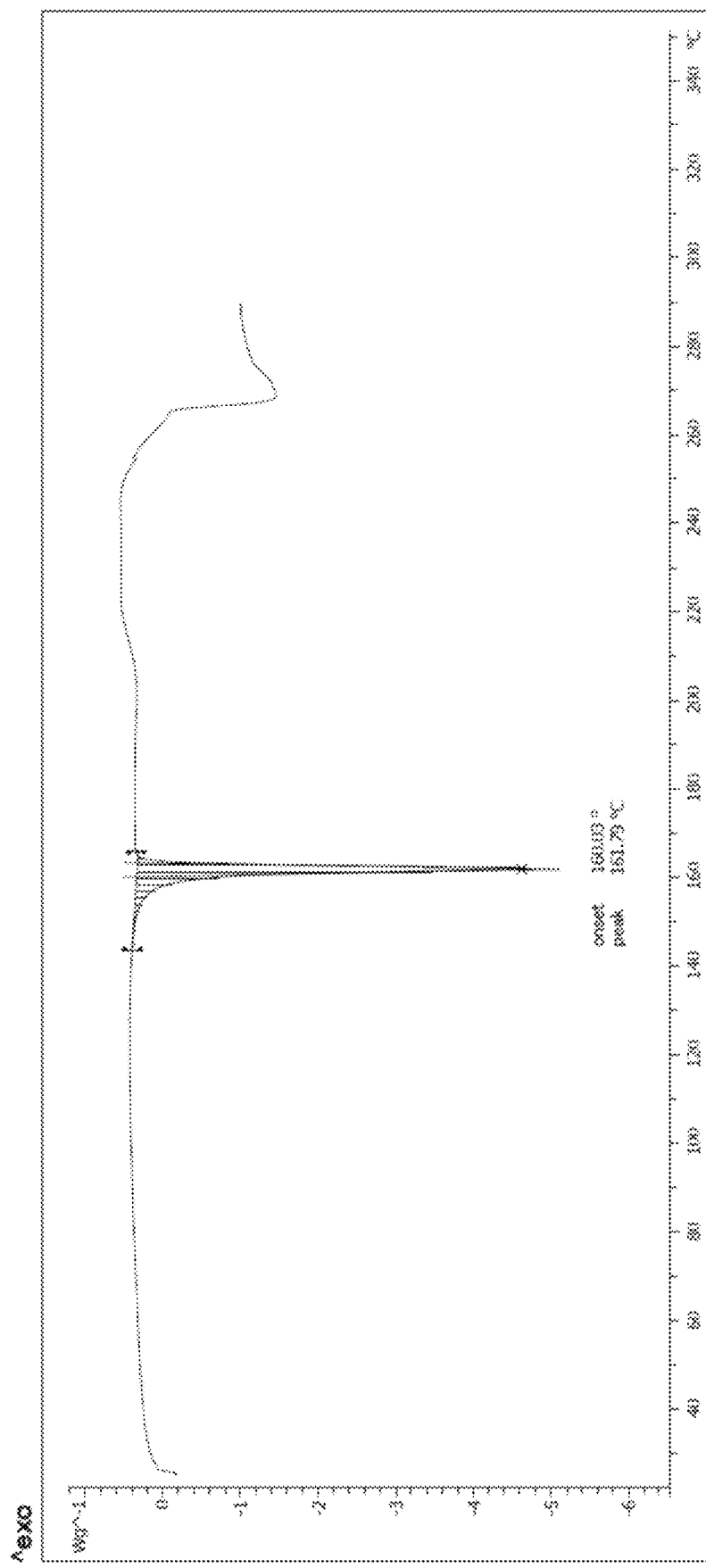

[Figure 8]
A.
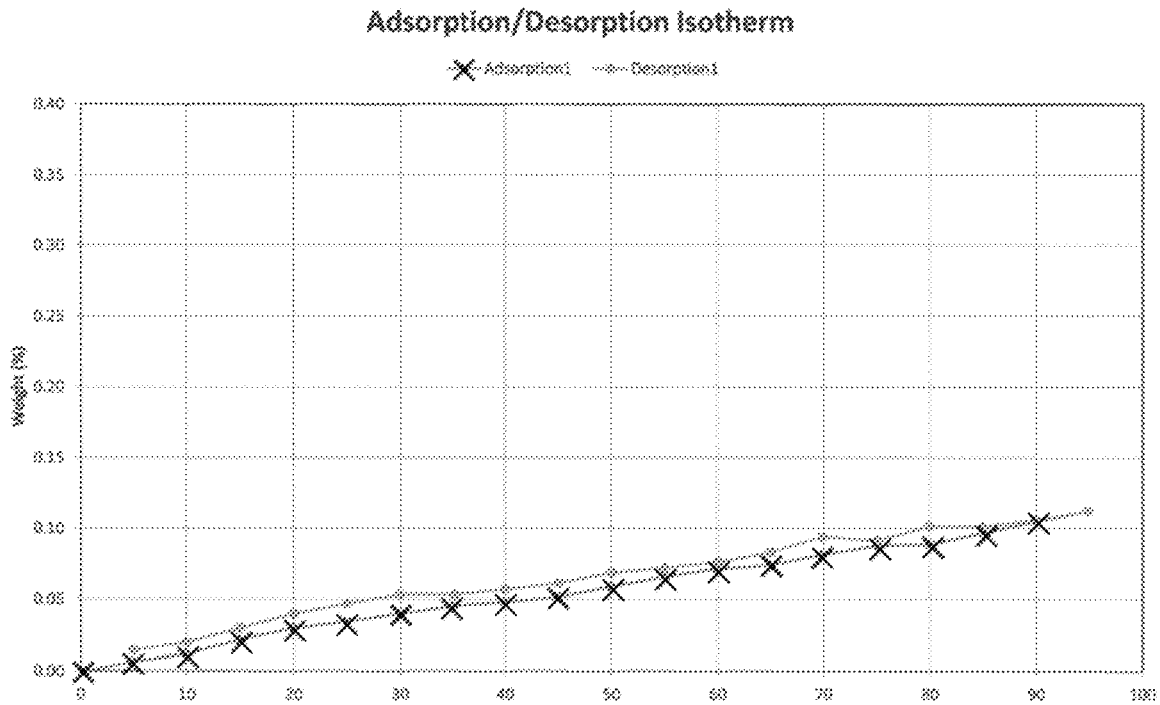
B.
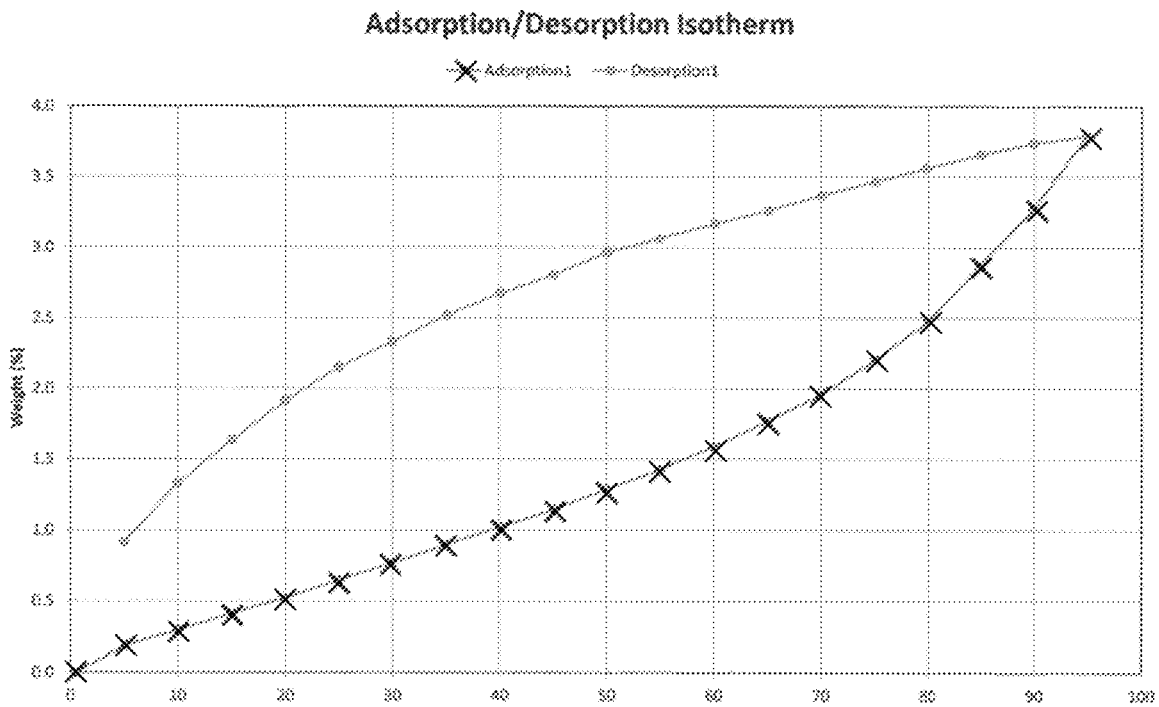

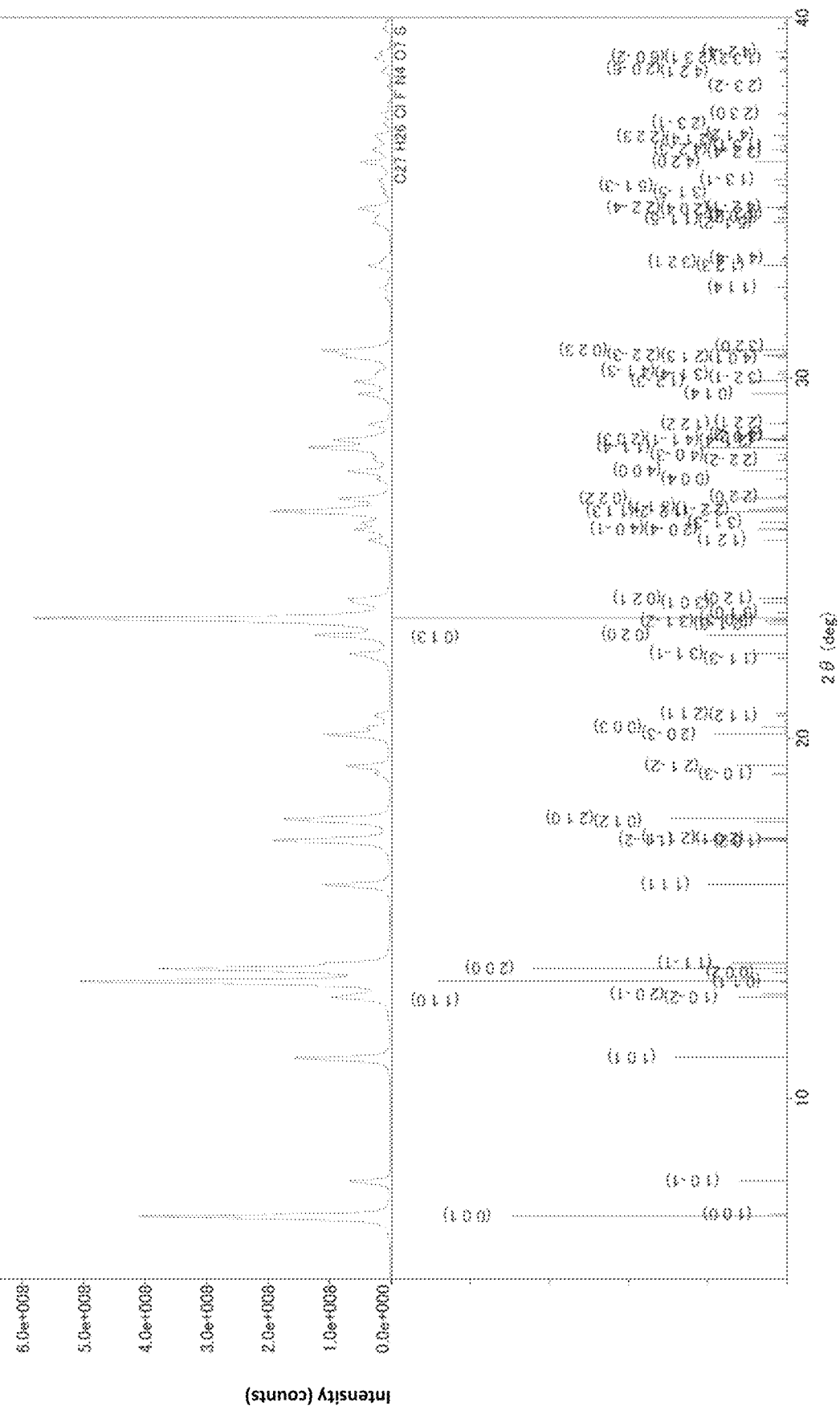
[Figure 9]

[Figure 10]
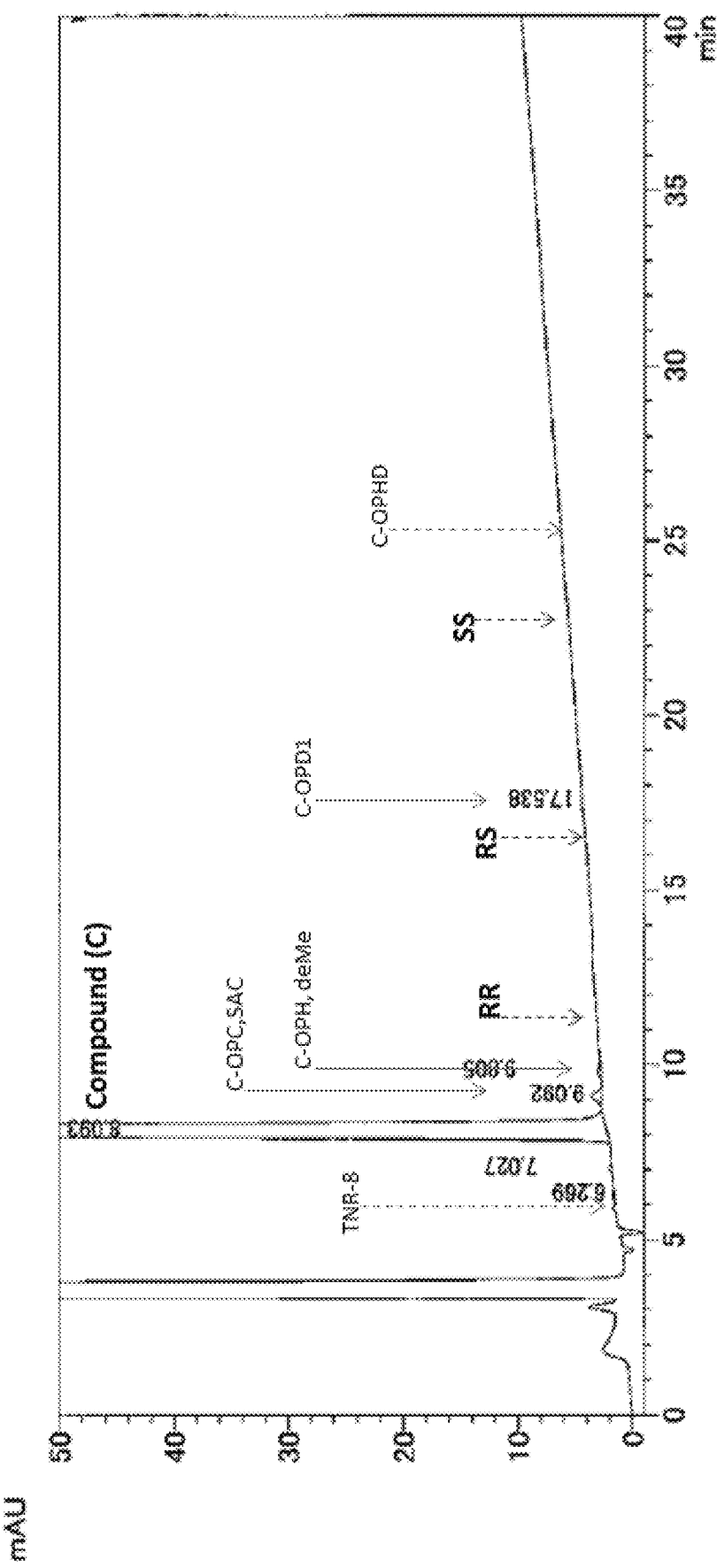

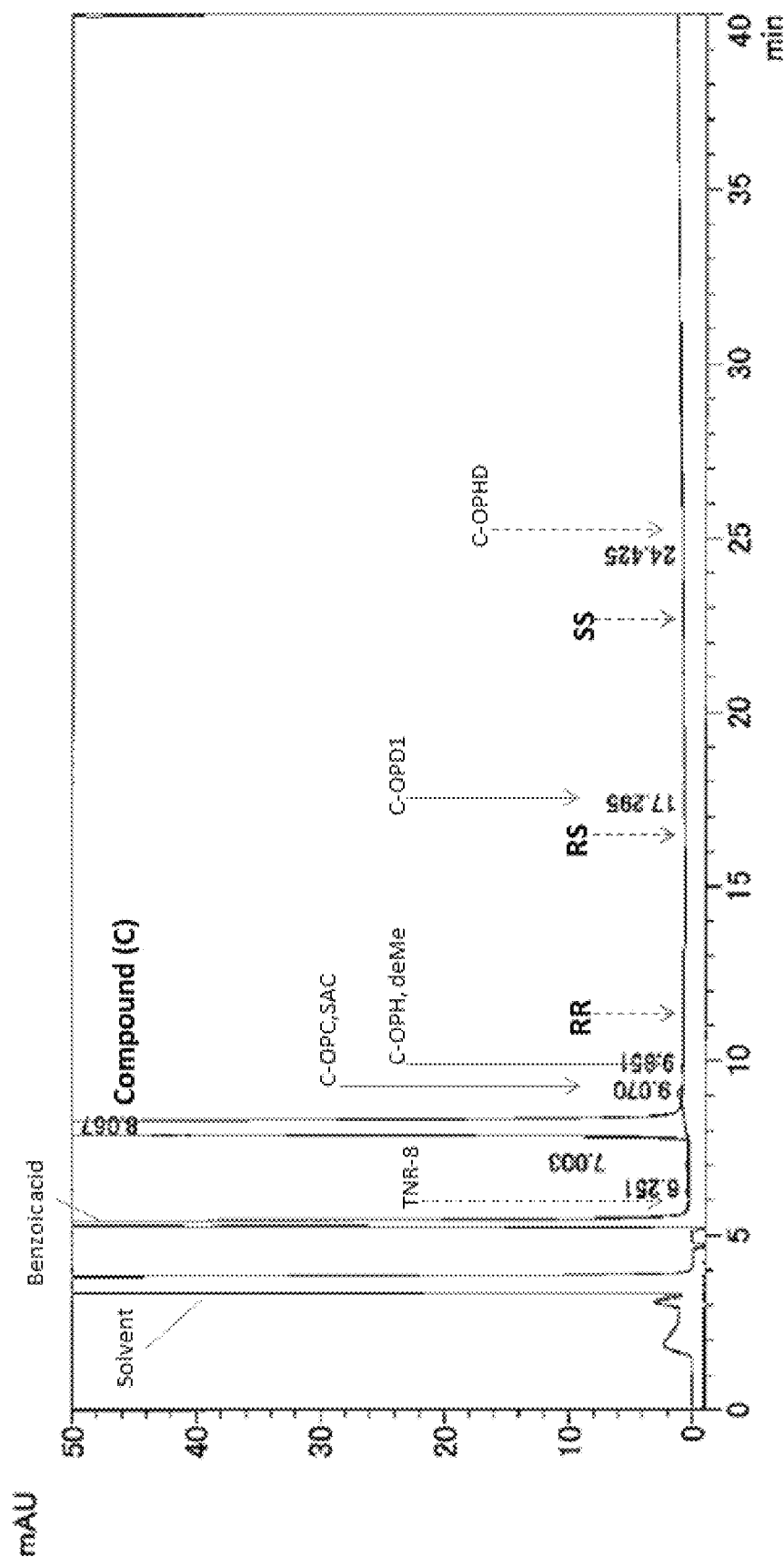
[Figure 11]

[Figure 12]
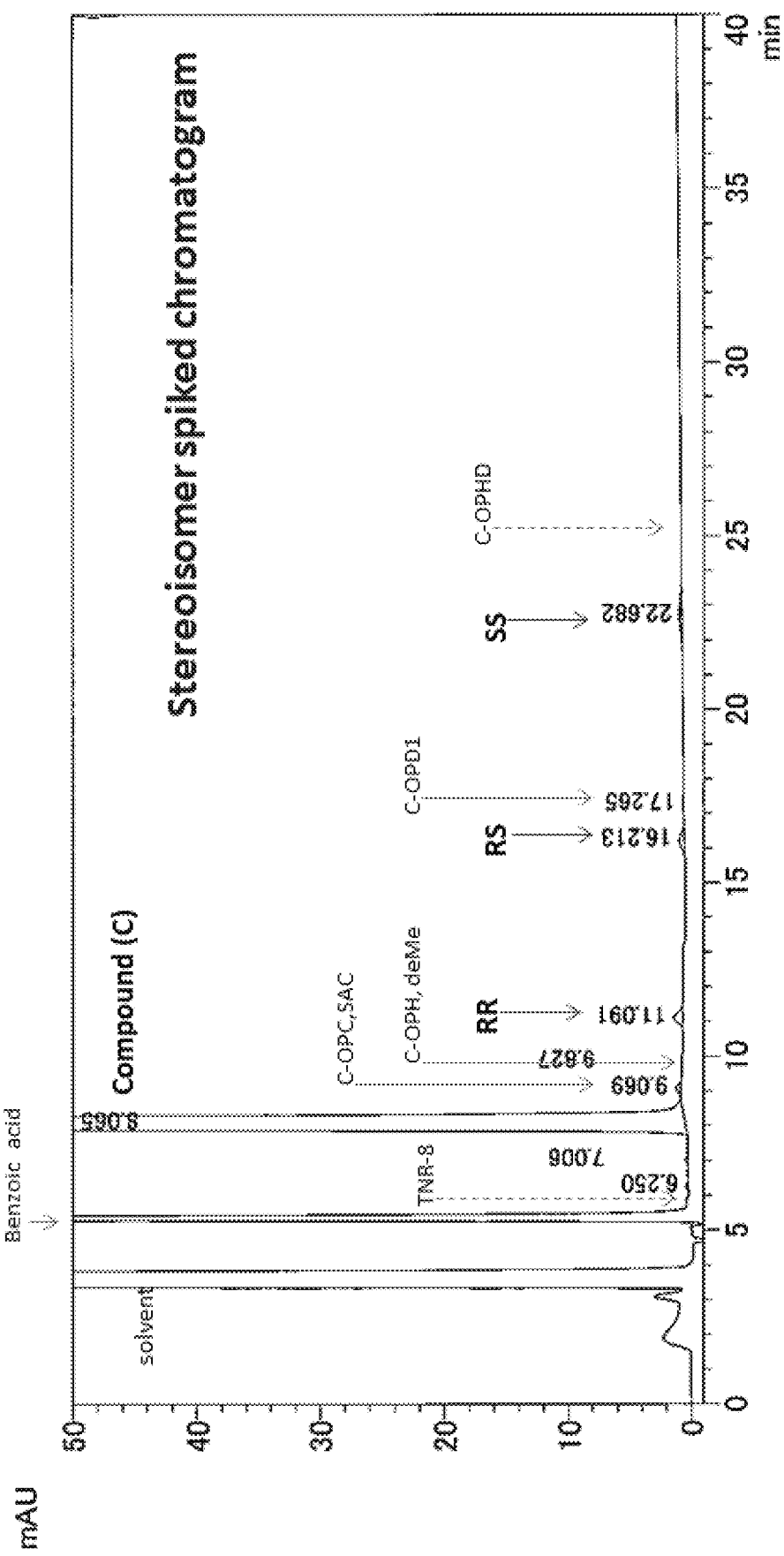

SULFONAMIDE COMPOUNDS AND USE THEREOF

TECHNICAL FIELD

The present disclosure relates to novel crystalline forms of sulfonamide compounds having ribonucleotide reductase inhibitory activity, pharmaceutical compositions containing the crystalline form compounds and methods of preparing and using the same.

BACKGROUND

Ribonucleotide reductase (hereinafter also referred to as "RNR") is composed of a hetero-oligomer of a large subunit M1 and a small subunit M2, where expression of both is required for enzyme activity. RNR recognizes ribonucleoside 5'-diphosphate (hereinafter also referred to as "NDP") as a substrate and catalyzes its reduction to 2'-deoxyribonucleoside 5'-diphosphate (hereinafter also referred to as "dNDP"). RNR is a rate-limiting enzyme in the de novo dNTP synthesis pathway and plays an essential role in DNA synthesis and repair.

The enzymatic activity of RNR is closely related to cell proliferation, and it has been reported that its enzymatic activity is particularly high in cancer. In various types of solid tumors and blood cancers, numerous correlations have been reported with overexpression of the M2 subunit of RNR, and its impact on the prognosis of the cancer. In addition, cell growth inhibition achieved by inhibition of RNR and an in vivo anti-tumor effect have been reported in cell lines derived from several cancer types and in nonclinical models. Thus, it is strongly suggested that RNR is an important target molecule for cancer treatment.

Conventionally, hydroxyurea (hereinafter also referred to as "HU") and 3-aminopyridine-2-carboxaldehyde thiosemicarbazone (hereinafter also referred to as "3-AP") are known to exhibit RNR inhibitory activity. These compounds differ in structure, however, from the sulfonamide compounds of the present disclosure. Although HU has been used clinically for over 30 years, its RNR inhibitory activity is weak and its effect is limited. Resistance to the use of HU is also considered a problem. 3-AP is capable of chelating to metal ions, especially iron (Fe) ions, thereby inhibiting RNR but 3-AP has been suggested as having an off-target effect on various other Fe ion-containing proteins, resulting in side effects such as hypoxia, dyspnea, methemoglobinemia and the like in clinical cases.

Therefore, there is a need to develop a potent RNR inhibitor which does not chelate with metal ions and can be used for the treatment of diseases associated with RNR, such as cancer.

In addition, there is a desire to develop an RNR inhibitor that can be easily handled. It is known that the chargeability and hygroscopicity of a biologically active compound affect the handling of the compound during its incorporation into a potential pharmaceutical composition. For example, active compounds that are subject to static electricity may create problems during manufacturing such as a reduced yield and uneven packaging. Thus, an active chemical compound having a low electrostatic charge is preferable. Hygroscopic compounds present problems due to their moisture absorption which leads to variations in compound mass depending on the amount of water present in the surrounding environment, making it difficult to accurately evaluate the compound's biological efficacy and to ensure the uniformity of pharmaceutical compositions containing the compound. Therefore, an active chemical compound with low hygroscopicity is desirable.

SUMMARY OF THE DISCLOSURE

One of the objectives of the present disclosure is to provide a novel, stable, and less static crystalline form, co-crystal and/or salt of a compound that is a potent and selective inhibitor of RNR and may be used as an antitumor agent or a therapeutic agent in the treatment of other diseases associated with RNR.

As a result of extensive studies to identify a chemical compound that satisfies the above-described requirements, the inventors of the present disclosure have discovered stable, low electrostatic and non-hygroscopic forms of sulfonamide compounds having excellent RNR inhibitory activity and use as a therapeutic agent for treating tumors and other diseases associated with RNR. These sulfonamide compounds exist as a crystalline form, such as co-crystals, and/or as a salt form.

Various aspects of the present disclosure provide the following sections [1] to [28].

[1] A crystalline form of a compound selected from the group consisting of:
5-bromo-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide;
5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide;
5-chloro-2-(N-((1S,2R)-2-(3-ethyl-6-fluoro-2-methylphenyl)-1-(5-oxo-4,5-dihydro-1,3,4-oxadiazol-2-yl)propyl)sulfamoyl)benzamide;
5-chloro-2-(N-((1S,2R)-2-(3-chloro-6-fluoro-2-methylphenyl)-1-(5-oxo-4,5-dihydro-1,3,4-oxadiazol-2-yl)propyl) sulfamoyl) benzamide;
5-chloro-N-((1S,2R)-2-(6-fluoro-2,3-dimethylphenyl)-1-(5-oxo-4,5-dihydro-1,3,4-oxadiazol-2-yl)propyl)-4-hydroxy-4-methyl-d3-chroman-8-sulfonamide;
5-chloro-N-((1S,2R)-2-(3-chloro-6-fluoro-2-methylphenyl)-1-(5-oxo-4,5-dihydro-1,3,4-oxadiazol-2-yl)propyl)-4-hydroxy-4-methylchroman-8-sulfonamide;
N-((1S,2R)-2-(3-bromo-6-fluoro-2-methylphenyl)-1-(5-oxo-4,5-dihydro-1,3,4-oxadiazol-2-yl)propyl)-5-chloro-4-hydroxy-4-methylchroman-8-sulfonamide;
5-chloro-N-((1S,2R)-2-(3-chloro-6-fluoro-2-methylphenyl)-1-(5-oxo-4,5-dihydro-1,3,4-oxadiazol-2-yl)propyl)-4-hydroxy-4-methyl-d3-chroman-8-sulfonamide; and
5-chloro-N-((1S,2R)-2-(6-fluoro-2,3-dimethylphenyl)-1-(5-oxo-4,5-dihydro-1,3,4-oxadiazol-2-yl)propyl)-4-hydroxychroman-8-sulfonamide.

[2] The crystalline form according to section [1], wherein the chemical purity of the crystalline form is 90% or more.

[3] The crystalline form according to section [1] or [2], wherein the optical purity of the crystalline form is 100% ee.

[4] The crystalline form according to any one of sections [1]-[3], wherein the crystalline form is stable upon exposure to conditions of about 40° C. and about 75% relative humidity for about four weeks.

[5] The crystalline form according to any one of sections [1]-[4], wherein the crystalline form further comprises benzoic acid.

[6] The crystalline form according to any one of sections [1]-[5], wherein the crystalline form is a co-crystal of benzoic acid and the compound.

[7] A pharmaceutical composition comprising (i) the crystalline form of any one of sections [1]-[6] and (ii) a pharmaceutically acceptable carrier.

[8] A method of inhibiting ribonucleotide reductase in vivo comprising administering to a human subject in need thereof a therapeutically effective amount of the pharmaceutical composition according to section [7]. In some embodiments, the inhibition of ribonucleotide reductase occurs in a tumor cell in the human subject.

[9] An anti-tumor agent comprising the crystalline form of any one of sections [1]-[6] as an active ingredient. In some embodiments, the anti-tumor agent is an oral anti-tumor agent.

[10] Use of the crystalline form of any one of sections [1]-[6] for manufacturing a ribonucleotide reductase inhibitor.

[11] Use of the crystalline form of any one of sections [1]-[6] as a medicament.

[12] Use of the crystalline form of any one of sections [1]-[6] as an anti-tumor agent. In some embodiments, the anti-tumor agent is an oral anti-tumor agent.

[13] The crystalline form of any one of sections [1]-[6] for use as a ribonucleotide reductase inhibitor.

[14] The crystalline form of any one of sections [1]-[6] for use in preventing or treating tumors.

[15] The crystalline form of any one of sections [1]-[6] for use in preventing or treating tumors by orally administering the compound.

[16] The crystalline form of any one of sections [1]-[6], wherein the compound or the benzoic acid may be substituted with one or more radioactive isotopes or a non-radioactive isotope.

[17] A benzoic acid salt of a compound selected from the group consisting of:
5-bromo-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide;
5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide;
5-chloro-2-(N-((1S,2R)-2-(3-ethyl-6-fluoro-2-methylphenyl)-1-(5-oxo-4,5-dihydro-1,3,4-oxadiazol-2-yl)propyl)sulfamoyl)benzamide;
5-chloro-2-(N-((1S,2R)-2-(3-chloro-6-fluoro-2-methylphenyl)-1-(5-oxo-4,5-dihydro-1,3,4-oxadiazol-2-yl)propyl)sulfamoyl) benzamide;
5-chloro-N-((1S,2R)-2-(6-fluoro-2,3-dimethylphenyl)-1-(5-oxo-4,5-dihydro-1,3,4-oxadiazol-2-yl)propyl)-4-hydroxy-4-methyl-d3-chroman-8-sulfonamide;
5-chloro-N-((1S,2R)-2-(3-chloro-6-fluoro-2-methylphenyl)-1-(5-oxo-4,5-dihydro-1,3,4-oxadiazol-2-yl)propyl)-4-hydroxy-4-methylchroman-8-sulfonamide; N-((1S,2R)-2-(3-bromo-6-fluoro-2-methylphenyl)-1-(5-oxo-4,5-dihydro-1,3,4-oxadiazol-2-yl)propyl)-5-chloro-4-hydroxy-4-methylchroman-8-sulfonamide;
5-chloro-N-((1S,2R)-2-(3-chloro-6-fluoro-2-methylphenyl)-1-(5-oxo-4,5-dihydro-1,3,4-oxadiazol-2-yl)propyl)-4-hydroxy-4-methyl-d3-chroman-8-sulfonamide; and
5-chloro-N-((1S,2R)-2-(6-fluoro-2,3-dimethylphenyl)-1-(5-oxo-4,5-dihydro-1,3,4-oxadiazol-2-yl)propyl)-4-hydroxychroman-8-sulfonamide.

[18] A pharmaceutical composition comprising (i) the benzoic acid salt of section [17] and (ii) a pharmaceutically acceptable carrier.

[19] A method of inhibiting ribonucleotide reductase in vivo comprising administering to a human subject in need thereof a therapeutically effective amount of the pharmaceutical composition according to section [18]. In some embodiments, the inhibition of ribonucleotide reductase occurs in a tumor cell in the human subject.

[20] An anti-tumor agent comprising the benzoic acid salt of section [17] as an active ingredient. In some embodiments, the anti-tumor agent is an oral anti-tumor agent.

[21] Use of the benzoic acid salt of section [17] for manufacturing a ribonucleotide reductase inhibitor.

[22] Use of the benzoic acid salt of section [17] as a medicament.

[23] Use of the benzoic acid salt of section [17] as an anti-tumor agent. In some embodiments, the anti-tumor agent is an oral anti-tumor agent.

[24] The benzoic acid salt of section [17] for use as a ribonucleotide reductase inhibitor.

[25] The benzoic acid salt of section [17] for use in preventing or treating tumors.

[26] The benzoic acid salt of section [17] for use in preventing or treating tumors by orally administering the compound.

[27] The benzoic acid salt of section [17], wherein the benzoic acid may be substituted with one or more radioactive isotope or a non-radioactive isotope.

The present disclosure relates to the crystalline forms of any one of sections [1]-[6], the co-crystals of section [6] and/or the benzoic acid salts of section [17] that act as RNR inhibitors.

The crystalline forms, co-crystals and/or benzoic acid salts of the present disclosure exhibit excellent RNR-inhibiting activity and stability and are also easy to handle because they are non-hygroscopic and/or non-electrostatic. Accordingly, the crystalline forms, co-crystals and/or benzoic acid salts described herein are suitable for use in the treatment of diseases associated with RNR.

BRIEF DESCRIPTION OF THE DRAWINGS

FIG. 1 depicts a diagram illustrating the daily variations in relative tumor volume (hereinafter also referred to as "RTV") after treatment with an exemplary compound disclosed herein.

FIG. 2 depicts a diagram illustrating the daily variations in RTV after treatment with an exemplary compound disclosed herein.

FIG. 3 depicts a diagram illustrating the daily variations in RTV after treatment with an exemplary compound disclosed herein.

FIG. 4 depicts a diagram illustrating the daily variations in RTV after treatment with an exemplary compound disclosed herein.

FIG. 5 depicts an exemplary crystalline form disclosed herein. The exemplary crystalline form had a crystal size of 0.15×0.20×0.25 mm, was colorless, and had plate shape.

FIG. 6 depicts a powder X-ray diffraction (XRD) chart of an exemplary co-crystal.

FIG. 7 depicts a differential scanning calorimetric (DSC) curve an exemplary co-crystal.

FIG. 8 depicts moisture adsorption/desorption isothermal curves of a co-crystal of an exemplary compound (A) and of a free form of the same compound (B).

FIG. 9 depicts an X-ray diffraction pattern simulation result based on a single crystal analysis result of an exemplary benzoic acid co-crystal.

FIGS. 10-12 depict optical purity measurement data of an exemplary crystalline form.

DETAILED DESCRIPTION OF THE DISCLOSURE

The present disclosure relates to crystalline forms, co-crystals or benzoic acid salts of a compound selected from the group consisting of:

5-bromo-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide;

5-chloro-2-(N-((1S,2R)-2-(2,3-dimethylphenyl)-1-(5-oxo-4,5-dihydro-1,3,4-oxadiazol-2-yl)propyl)sulfamoyl)benzamide;

5-bromo-2-(N-((1S,2R)-2-(2,3-dimethylphenyl)-1-(5-oxo-4,5-dihydro-1,3,4-oxadiazol-2-yl)propyl)sulfamoyl)benzamide;

5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide 5-chloro-2-(N-(1S,2R)-2-(2-fluoronaphtalene-1-yl)-1-(5-oxo-4,5-dihydro-1,3,4-oxadiazol-2-yl)propyl) sulfamoyl) benzamide;

5-chloro-2-(N-((1S,2R)-2-(3-ethyl-6-fluoro-2-methylphenyl)-1-(5-oxo-4,5-dihydro-1,3,4-oxadiazol-2-yl)propyl)sulfamoyl)benzamide;

5-chloro-2-(N-((1S,2R)-2-(3-chloro-6-fluoro-2-methylphenyl)-1-(5-oxo-4,5-dihydro-1,3,4-oxadiazol-2-yl)propyl) sulfamoyl) benzamide;

5-bromo-2-(N-((1S,2R)-2-(3-chloro-6-fluoro-2-methylphenyl)-1-(5-oxo-4,5-dihydro-1,3,4-oxadiazol-2-yl)propyl) sulfamoyl)benzamide; 2-(N-((1S,2R)-2-(3-bromo-6-fluoro-2-methylphenyl)-1-(5-oxo-4,5-dihydro-1,3,4-oxadiazol-2-yl)propyl)sulfamoyl)-5-chloro-benzamide;

5-chloro-N-((1S,2R)-2-(6-fluoro-2,3-dimethylphenyl)-1-(5-oxo-4,5-dihydro-1,3,4-oxadiazol-2-yl)propyl)-6-(pyrrolidine-1-carbonyl)pyridine-2-sulfonamide;

5-chloro-N-((1S,2R)-2-(6-fluoro-2,3-dimethylphenyl)-1-(5-oxo-4,5-dihydro-1,3,4-oxadiazol-2-yl)propyl)-4-hydroxy-4-methyl-d3-chroman-8-sulfonamide;

5-chloro-N-((1S,2R)-2-(3-chloro-6-fluoro-2-methylphenyl)-1-(5-oxo-4,5-dihydro-1,3,4-oxadiazol-2-yl)propyl)-4-hydroxy-4-methylchroman-8-sulfonamide;

N-((1S,2R)-2-(3-bromo-6-fluoro-2-methylphenyl)-1-(5-oxo-4,5-dihydro-1,3,4-oxadiazol-2-yl)propyl)-5-chloro-4-hydroxy-4-methylchroman-8-sulfonamide;

5-Chloro-N-((1S,2R)-2-(3-chloro-6-fluoro-2-methylphenyl)-1-(5-oxo-4,5-dihydro-1,3,4-oxadiazol-2-yl)propyl)-4-hydroxy-4-methyl-d3-chroman-8-sulfonamide;

5-chloro-N-((1S,2R)-2-(6-fluoro-2,3-dimethylphenyl)-1-(5-oxo-4,5-dihydro-1,3,4-oxadiazol-2-yl)propyl)-4-hydroxychroman-8-sulfonamide;

3-Chloro-6-(N-((1S,2R)-2-(6-fluoro-2,3-dimethylphenyl)-1-(5-oxo-4,5-dihydro-1,3,4-oxadiazol-2-yl)propyl)sulfamoyl)-N, N-dimethylpicolinamide;

4-Amino-2-methoxy-N-((1S,2R)-2-(8-methylnaphthalene-1-yl)-1-(5-oxo-4,5-dihydro-1,3,4-oxadiazol-2-yl)propyl)benzenesulfonamide;

4-Amino-N-((1S,2R)-2-(2,3-dihydro-1H-indene-4-yl)-1-(5-oxo-4,5-dihydro-1,3,4-oxadiazol-2-yl)propyl)-2-methoxybenzenesulfonamide; and 5-chloro-2-(((1S,2R)-methyl-d3-2-(6-fluoro-2,3-dimethylphenyl)-1-(5-oxo-4,5-dihydro-1,3,4-oxadiazol-2-yl)propyl)sulfamoyl)benzamide.

In some embodiments, the compound is selected from the group consisting of:

5-bromo-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide;

5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide;

5-chloro-2-(N-((1S,2R)-2-(3-ethyl-6-fluoro-2-methylphenyl)-1-(5-oxo-4,5-dihydro-1,3,4-oxadiazol-2-yl)propyl)sulfamoyl)benzamide;

5-chloro-2-(N-((1S,2R)-2-(3-chloro-6-fluoro-2-methylphenyl)-1-(5-oxo-4,5-dihydro-1,3,4-oxadiazol-2-yl)propyl) sulfamoyl) benzamide;

5-chloro-N-((1S,2R)-2-(6-fluoro-2,3-dimethylphenyl)-1-(5-oxo-4,5-dihydro-1,3,4-oxadiazol-2-yl)propyl)-4-hydroxy-4-methyl-d3-chroman-8-sulfonamide;

5-chloro-N-((1S,2R)-2-(3-chloro-6-fluoro-2-methylphenyl)-1-(5-oxo-4,5-dihydro-1,3,4-oxadiazol-2-yl)propyl)-4-hydroxy-4-methylchroman-8-sulfonamide;

N-((1S,2R)-2-(3-bromo-6-fluoro-2-methylphenyl)-1-(5-oxo-4,5-dihydro-1,3,4-oxadiazol-2-yl)propyl)-5-chloro-4-hydroxy-4-methylchroman-8-sulfonamide;

5-chloro-N-((1S,2R)-2-(3-chloro-6-fluoro-2-methylphenyl)-1-(5-oxo-4,5-dihydro-1,3,4-oxadiazol-2-yl)propyl)-4-hydroxy-4-methyl-d3-chroman-8-sulfonamide; and 5-chloro-N-((1S,2R)-2-(6-fluoro-2,3-dimethylphenyl)-1-(5-oxo-4,5-dihydro-1,3,4-oxadiazol-2-yl)propyl)-4-hydroxychroman-8-sulfonamide.

In additional embodiments, the compound is selected from the group consisting of:

5-bromo-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide;

5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide;

5-chloro-2-(N-((1S,2R)-2-(3-chloro-6-fluoro-2-methylphenyl)-1-(5-oxo-4,5-dihydro-1,3,4-oxadiazol-2-yl)propyl) sulfamoyl) benzamide;

5-chloro-N-((1S,2R)-2-(3-chloro-6-fluoro-2-methylphenyl)-1-(5-oxo-4,5-dihydro-1,3,4-oxadiazol-2-yl)propyl)-4-hydroxy-4-methylchroman-8-sulfonamide; and 5-chloro-N-((1S,2R)-2-(6-fluoro-2,3-dimethylphenyl)-1-(5-oxo-4,5-dihydro-1,3,4-oxadiazol-2-yl)propyl)-4-hydroxychroman-8-sulfonamide.

In some embodiments, the compound is 5-bromo-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide. In some embodiments, the present disclosure relates to the crystalline form of 5-bromo-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide, or the co-crystal of benzoic acid and the compound.

In some embodiments, the compound is 5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide. In some embodiments, the present disclosure relates to the crystalline forms of 5-chloro-2-(N-((1S,2R)-2-(6-fluoro-2, 3-dimethylphenyl)-1-(5-oxo-4,5-dihydro-1,3,4-oxadiazol-2-yl)propyl)sulfamoyl)benzamide, or the co-crystal of benzoic acid and the compound.

In some embodiments, the compound is 5-chloro-2-(N-((1S,2R)-2-(3-chloro-6-fluoro-2-methylphenyl)-1-(5-oxo-4, 5-dihydro-1,3,4-oxadiazol-2-yl)propyl) sulfamoyl) benzamide. In some embodiments, the present disclosure relates to the crystalline form of 5-chloro-2-(N-((1S,2R)-2-(3-chloro-6-fluoro-2-methylphenyl)-1-(5-oxo-4,5-dihydro-1,3, 4-oxadiazol-2-yl)propyl) sulfamoyl) benzamide, or the co-crystal of benzoic acid and the compound.

In some embodiments, the compound is 5-chloro-N-((1S, 2R)-2-(3-chloro-6-fluoro-2-methylphenyl)-1-(5-oxo-4,5-dihydro-1,3,4-oxadiazol-2-yl)propyl)-4-hydroxy-4-methyl-chroman-8-sulfonamide. In some embodiments, the present disclosure relates to the crystalline form of 5-chloro-N-((1S,2R)-2-(3-chloro-6-fluoro-2-methylphenyl)-1-(5-oxo-4,5-dihydro-1,3,4-oxadiazol-2-yl)propyl)-4-hydroxy-4-methyl-chroman-8-sulfonamide, or the co-crystal of benzoic acid and the compound.

In some embodiments, the compound is 5-chloro-N-((1S,2R)-2-(6-fluoro-2,3-dimethylphenyl)-1-(5-oxo-4,5-dihydro-1,3,4-oxadiazol-2-yl)propyl)-4-hydroxychroman-8-sulfonamide. In some embodiments, the present disclosure relates to the crystalline form of 5-chloro-N-((1S,2R)-2-(6-fluoro-2,3-dimethylphenyl)-1-(5-oxo-4,5-dihydro-1,3,4-oxadiazol-2-yl)propyl)-4-hydroxychroman-8-sulfonamide, or the co-crystal of benzoic acid and the compound.

The crystalline form compounds, co-crystals and/or benzoic acid salts of the present disclosure and intermediates thereof can be isolated and purified by well-known separation and purification techniques such as recrystallization, crystallization, distillation and column chromatography.

When optical isomers, stereoisomers, tautomers, or rotary isomers are possible in the crystalline form compounds, co-crystals or benzoic acid salts of the present disclosure but not explicitly depicted, the crystalline form compounds, co-crystals and/or benzoic acid salts are intended to encompass these isomers separately or as mixtures thereof. For example, unless otherwise stated, when a crystalline form compound, co-crystal and/or benzoic acid salt of the present disclosure appears as the racemate, the possible enantiomers and/or diastereomers that can be resolved from the racemate are also considered to be encompassed by of the present disclosure. The enantiomers and/or diastereomers can typically be obtained by well-known synthetic methods.

As used herein and unless otherwise specified, the term "crystal" and related terms used herein, when used to describe a compound, substance, modification, material, component or product, mean that the compound, substance, modification, material, component or product is substantially crystalline as determined by X-ray diffraction. See, e.g., Remington: The Science and Practice of Pharmacy, 21$^{st}$ edition, Lippincott, Williams and Wilkins, Baltimore, MD (2005); The United States Pharmacopeia, 23$^{rd}$ ed. 1843-1844 (1995).

As used herein and unless otherwise specified, the term "crystalline form" and related terms herein refer to solid forms that are crystalline. Crystalline forms include single-component crystalline forms and multiple-component crystalline forms, and may optionally include, but are not limited to, co-crystals, salts (including pharmaceutically acceptable salts), polymorphs, solvates, hydrates, and/or other molecular complexes. In certain embodiments, a crystalline form of a substance may be substantially free of amorphous forms and/or other crystalline forms. In certain embodiments, a crystalline form of a substance may contain less than about 0.1, 0.5, 1, 2, 3, 4, 5, 6, 7, 8, 9, 10, 11, 12, 13, 14, 15, 20, 25, 30, 35, 40, 45 or 50% of one or more amorphous forms and/or other crystalline forms on a weight basis.

The term "co-crystal" refers to a molecular complex derived from a number of co-crystal formers known in the art. Unlike a salt, a co-crystal typically does not involve hydrogen transfer between the co-crystal former and the drug, and instead involves intermolecular interactions, such as hydrogen bonding, aromatic ring stacking, or dispersive forces, between the co-crystal former and the sulfonamide compound in the crystal structure. In some embodiments, the present disclosure relates to a co-crystal comprising or consisting of benzoic acid and a sulfonamide compound as described herein.

As used herein and unless otherwise specified, the terms "polymorphs," "polymorphic forms" and related terms herein, refer to two or more crystalline forms that consist essentially of the same molecule, molecules, and/or ions. Like different crystalline forms, different polymorphs may have different physical properties such as, e.g., melting temperature, heat of fusion, solubility, dissolution properties and/or vibrational spectra, as a result of the arrangement or conformation of the molecules and/or ions in the crystal lattice. The differences in physical properties may affect pharmaceutical parameters such as storage stability, compressibility and density (important in formulation and product manufacturing), and dissolution rate (an important factor in bioavailability). Differences in stability can result from changes in chemical reactivity (e.g., differential oxidation, such that a dosage form discolors more rapidly when comprised of one polymorph than when comprised of another polymorph) or mechanical changes (e.g., tablets crumble on storage as a kinetically favored polymorph converts to thermodynamically more stable polymorph) or both (e.g., tablets of one polymorph are more susceptible to breakdown at high humidity). As a result of solubility/dissolution differences, in the extreme case, some solid-state transitions may result in lack of potency or, at the other extreme, toxicity. In addition, the physical properties may be important in processing (e.g., one polymorph might be more likely to form solvates or might be difficult to filter and wash free of impurities, and particle shape and size distribution might be different between polymorphs).

As used herein and unless otherwise specified, the term "amorphous," "amorphous form," and related terms used herein, mean that the substance, component or product in question is not substantially crystalline as determined by X-ray diffraction. In particular, the term "amorphous form" describes a disordered solid form, i.e., a solid form lacking long range crystalline order.

The term "pharmaceutically acceptable salt" refers to salts derived from a variety of organic and inorganic counter ions known in the art. The pharmaceutically acceptable salt may be safe for animal or human consumption.

In one aspect, the disclosure relates to a crystalline form of a sulfonamide compound as described above. In some embodiments, a structure of a crystal of a sulfonamide compound disclosed herein comprises a lath, plate, and/or planar crystal structure.

Techniques for characterizing crystalline forms and amorphous forms include, but are not limited to, thermal gravimetric analysis (TGA), differential scanning calorimetry (DSC), X-ray powder diffractometry (XRPD), single-crystal X-ray diffractometry, vibrational spectroscopy, e.g., infrared (IR) and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility measurements, dissolution measurements, elemental analysis, and Karl Fischer analysis. Characteristic unit cell parameters may be determined using one or more techniques such as, but not limited to, X-ray diffraction and neutron diffraction, including single-crystal diffraction and powder diffraction. Techniques useful for analyzing powder diffraction data include profile refinement, such as Rietveld refinement, which may be used, e.g., to analyze diffraction peaks associated with a single phase in a sample comprising more than one solid phase. Other methods useful for analyzing powder diffraction data include unit cell indexing, which allows one skilled in the art to determine unit cell parameters from a sample comprising crystalline powder.

In the powder X-ray diffraction spectrum, the diffraction angle and the overall pattern may be important in identifying the identity of the crystal due to the nature of the data. The relative intensity of the powder X-ray diffraction spectrum may vary depending on the direction of crystal growth, particle size, or measurement conditions and thus should not be strictly interpreted. In addition, some values obtained from various patterns may cause some errors depending on the direction of crystal growth, particle size, measurement conditions, and the like. For example, the diffraction angle may be a diffraction angle (2θ±0.2°) in the powder X-ray diffraction spectrum, which means that the diffraction angle may separately be within ±0.2° of any particular value unless otherwise indicated.

In some embodiments, the disclosure relates to a crystalline form of 5-bromo-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide. In additional embodiments, the X-ray diffraction pattern of this crystalline form has two or more, three or more, four or more, five or more, six or more, seven or more, eight or more, or nine peaks at (2θ±0.2, 0.3, 0.4, 0.5, 0.6, 0.7, 0.8, 0.9 or 1.0°) of 6.8°, 7.8°, 11.2°, 13.4°, 13.7°, 16.0°, 17.1°, 17.8° and 23.2°. In further embodiments, the crystalline form of 5-bromo-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide has an endothermic peak from about 154, 155, 156, 157, 158, 159, 160, or 161° C. to about 160, 161, 162, 163, 164, 165, 166, 167, 168, 169 or 170° C. as measured by DSC. In some embodiments, the crystalline form of 5-bromo-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide has an endothermic peak from 155° C. to 168° C., from 158° C. to 162° C., from 159° C. to 161° C., from 159° C. to 165° C., or from 160° C. to 163° C. as measured by DSC. In additional embodiments, the crystalline form of 5-bromo-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide has an endothermic peak of about 154, 155, 156, 157, 158, 159, 160, 161, 162, 163, 164, 165, 166, 167, 168, 169, or 170° C. measured by DSC. In additional embodiments, the optical purity of this crystalline form is 100% ee.

In some embodiments, the disclosure relates to a crystalline form of 5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide. In additional embodiments, the X-ray diffraction pattern of this crystalline form has two or more, three or more, four or more, five or more, six or more, seven or more, eight or more, or nine peaks at (2θ±0.2, 0.3, 0.4, 0.5, 0.6, 0.7, 0.8, 0.9 or 1.0°) of 6.8°, 7.8°, 11.2°, 13.4°, 13.7°, 16.0°, 17.1°, 17.8° and 23.2°. In further embodiments, the crystalline form of 5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide has an endothermic peak from about 154, 155, 156, 157, 158, 159, 160, or 161° C. to about 160, 161, 162, 163, 164, 165, 166, 167, 168, 169 or 170° C. as measured by DSC. In some embodiments, the crystalline form of 5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide has an endothermic peak from 155° C. to 168° C., from 158° C. to 162° C., from 159° C. to 161° C., from 159° C. to 165° C., or from 160° C. to 163° C. as measured by DSC. In additional embodiments, the crystalline form of 5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide has an endothermic peak of about 154, 155, 156, 157, 158, 159, 160, 161, 162, 163, 164, 165, 166, 167, 168, 169, or 170° C. measured by DSC. In additional embodiments, the optical purity of this crystalline form is 100% ee.

In some embodiments, the disclosure relates to a crystalline form of 5-chloro-2-(N-((1S,2R)-2-(3-ethyl-6-fluoro-2-methylphenyl)-1-(5-oxo-4,5-dihydro-1,3,4-oxadiazol-2-yl)propyl)sulfamoyl)benzamide. In additional embodiments, the X-ray diffraction pattern of this crystalline form has two or more, three or more, four or more, five or more, six or more, seven or more, eight or more, or nine peaks at (2θ±0.2, 0.3, 0.4, 0.5, 0.6, 0.7, 0.8, 0.9 or 1.0°) of 6.8°, 7.8°, 11.2°, 13.4°, 13.7°, 16.0°, 17.1°, 17.8° and 23.2°. In further embodiments, the crystalline form of 5-chloro-2-(N-((1S,2R)-2-(3-ethyl-6-fluoro-2-methylphenyl)-1-(5-oxo-4,5-dihydro-1,3,4-oxadiazol-2-yl)propyl)sulfamoyl)benzamide has an endothermic peak from about 154, 155, 156, 157, 158, 159, 160, or 161° C. to about 160, 161, 162, 163, 164, 165, 166, 167, 168, 169 or 170° C. as measured by DSC. In some embodiments, the crystalline form of 5-chloro-2-(N-((1S,2R)-2-(3-ethyl-6-fluoro-2-methylphenyl)-1-(5-oxo-4,5-dihydro-1,3,4-oxadiazol-2-yl)propyl)sulfamoyl)benzamide has an endothermic peak from 155° C. to 168° C., from 158° C. to 162° C., from 159° C. to 161° C., from 159° C. to 165 C, or from 160° C. to 163° C. as measured by DSC. In additional embodiments, the crystalline form of 5-chloro-2-(N-((1S,2R)-2-(3-ethyl-6-fluoro-2-methylphenyl)-1-(5-oxo-4,5-dihydro-1,3,4-oxadiazol-2-yl)propyl)sulfamoyl)benzamide has an endothermic peak of about 154, 155, 156, 157, 158, 159, 160, 161, 162, 163, 164, 165, 166, 167, 168, 169, or 170° C. measured by DSC. In additional embodiments, the optical purity of this crystalline form is 100% ee.

In some embodiments, the disclosure relates to a co-crystal of benzoic acid and 5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide. In additional embodiments, the X-ray diffraction pattern of this co-crystal has two or more, three or more, four or more, five or more, six or more, seven or more, eight or more, or nine peaks at (2θ±0.2, 0.3, 0.4, 0.5, 0.6, 0.7, 0.8, 0.9 or 1.0°) of 6.8°, 7.8°, 11.2°, 13.4°, 13.7°, 16.0°, 17.1°, 17.8° and 23.2°. In further embodiments, this co-crystal has an endothermic peak from about 154, 155, 156, 157, 158, 159, 160, or 161° C. to about 160, 161, 162, 163, 164, 165, 166, 167, 168, 169 or 170° C. as measured by DSC. In some embodiments, the co-crystal of benzoic acid of 5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide has an endothermic peak from 155° C. to 168° C., from 158° C. to 162° C., from 159° C. to 161° C., from 159° C. to 165° C., or from 160° C. to 163° C. as measured by DSC. In additional embodiments, this co-crystal has an endothermic peak of about 154, 155, 156, 157, 158, 159, 160, 161, 162, 163, 164, 165, 166, 167, 168, 169, or 170° C. measured by DSC. In additional embodiments, the optical purity of this co-crystal of benzoic acid is 100% ee.

In some embodiments, the disclosure relates to a crystalline form of 5-chloro-2-(N-((1S,2R)-2-(3-chloro-6-fluoro-2-methylphenyl)-1-(5-oxo-4,5-dihydro-1,3,4-oxadiazol-2-yl)propyl) sulfamoyl) benzamide. In additional embodiments, the X-ray diffraction pattern of this crystalline form has two or more, three or more, four or more, five or more, six or more, seven or more, eight or more, or nine peaks at (2θ±0.2, 0.3, 0.4, 0.5, 0.6, 0.7, 0.8, 0.9 or 1.0°) of 6.8°, 7.8°, 11.2°, 13.4°, 13.7°, 16.0°, 17.1°, 17.8° and 23.2°. In further embodiments, the crystalline form of 5-chloro-2-(N-((1S, 2R)-2-(3-chloro-6-fluoro-2-methylphenyl)-1-(5-oxo-4,5-dihydro-1,3,4-oxadiazol-2-yl)propyl) sulfamoyl) benzamide has an endothermic peak from about 154, 155, 156, 157, 158, 159, 160, or 161° C. to about 160, 161, 162, 163, 164, 165, 166, 167, 168, 169 or 170° C. as measured by DSC. In some embodiments, the crystalline form of 5-chloro-2-(N-((1S,2R)-2-(3-chloro-6-fluoro-2-methylphenyl)-1-(5-oxo-4, 5-dihydro-1,3,4-oxadiazol-2-yl)propyl) sulfamoyl) benzamide has an endothermic peak from 155° C. to 168° C., from 158° C. to 162° C., from 159° C. to 161° C., from 159° C. to 165° C., or from 160° C. to 163° C. as measured by DSC. In additional embodiments, the crystalline form of 5-chloro-2-(N-((1S,2R)-2-(3-chloro-6-fluoro-2-methylphenyl)-1-(5-oxo-4,5-dihydro-1,3,4-oxadiazol-2-yl)propyl) sulfamoyl) benzamide has an endothermic peak of about 154, 155, 156, 157, 158, 159, 160, 161, 162, 163, 164, 165, 166, 167, 168, 169, or 170° C. measured by DSC. In additional embodiments, the optical purity of this crystalline form is 100% ee.

In some embodiments, the disclosure relates to a crystalline form of 5-chloro-N-((1S,2R)-2-(6-fluoro-2,3-dimethylphenyl)-1-(5-oxo-4,5-dihydro-1,3,4-oxadiazol-2-yl)propyl)-4-hydroxy-4-methyl-d3-chroman-8-sulfonamide. In additional embodiments, the X-ray diffraction pattern of this crystalline form has two or more, three or more, four or more, five or more, six or more, seven or more, eight or more, or nine peaks at (2θ±0.2, 0.3, 0.4, 0.5, 0.6, 0.7, 0.8, 0.9 or 1.0°) of 6.8°, 7.8°, 11.2°, 13.4°, 13.7°, 16.0°, 17.1°, 17.8° and 23.2°. In further embodiments, the crystalline form of 5-chloro-N-((1S,2R)-2-(6-fluoro-2,3-dimethylphenyl)-1-(5-oxo-4,5-dihydro-1,3,4-oxadiazol-2-yl)propyl)-4-hydroxy-4-methyl-d3-chroman-8-sulfonamide has an endothermic peak from about 154, 155, 156, 157, 158, 159, 160, or 161° C. to about 160, 161, 162, 163, 164, 165, 166, 167, 168, 169 or 170° C. as measured by DSC. In some embodiments, the crystalline form of 5-chloro-N-((1S,2R)-2-(6-fluoro-2,3-dimethylphenyl)-1-(5-oxo-4,5-dihydro-1,3,4-oxadiazol-2-yl) propyl)-4-hydroxy-4-methyl-d3-chroman-8-sulfonamide has an endothermic peak from 155° C. to 168° C., from 158° C. to 162° C., from 159° C. to 161° C., from 159° C. to 165° C., or from 160° C. to 163° C. as measured by DSC. In additional embodiments, the crystalline form of 5-chloro-N-((1S,2R)-2-(6-fluoro-2,3-dimethylphenyl)-1-(5-oxo-4,5-dihydro-1,3,4-oxadiazol-2-yl)propyl)-4-hydroxy-4-methyl-d3-chroman-8-sulfonamide has an endothermic peak of about 154, 155, 156, 157, 158, 159, 160, 161, 162, 163, 164, 165, 166, 167, 168, 169, or 170° C. measured by DSC. In additional embodiments, the optical purity of this crystalline form is 100% ee.

In some embodiments, the disclosure relates to a crystalline form of 5-chloro-N-((1S,2R)-2-(3-chloro-6-fluoro-2-methylphenyl)-1-(5-oxo-4,5-dihydro-1,3,4-oxadiazol-2-yl) propyl)-4-hydroxy-4-methylchroman-8-sulfonamide. In additional embodiments, the X-ray diffraction pattern of this crystalline form has two or more, three or more, four or more, five or more, six or more, seven or more, eight or more, or nine peaks at (2θ±0.2, 0.3, 0.4, 0.5, 0.6, 0.7, 0.8, 0.9 or 1.0°) of 6.8°, 7.8°, 11.2°, 13.4°, 13.7°, 16.0°, 17.1°, 17.8° and 23.2°. In further embodiments, the crystalline form of 5-chloro-N-((1S,2R)-2-(3-chloro-6-fluoro-2-methylphenyl)-1-(5-oxo-4,5-dihydro-1,3,4-oxadiazol-2-yl)propyl)-4-hydroxy-4-methylchroman-8-sulfonamide has an endothermic peak from about 154, 155, 156, 157, 158, 159, 160, or 161° C. to about 160, 161, 162, 163, 164, 165, 166, 167, 168, 169 or 170° C. as measured by DSC. In some embodiments, the crystalline form of 5-chloro-N-((1S,2R)-2-(3-chloro-6-fluoro-2-methylphenyl)-1-(5-oxo-4,5-dihydro-1,3,4-oxadiazol-2-yl)propyl)-4-hydroxy-4-methylchroman-8-sulfonamide has an endothermic peak from 155° C. to 168° C., from 158° C. to 162° C., from 159° C. to 161° C., from 159° C. to 165° C., or from 160° C. to 163° C. as measured by DSC. In additional embodiments, the crystalline form of 5-chloro-N-((1S,2R)-2-(3-chloro-6-fluoro-2-methylphenyl)-1-(5-oxo-4,5-dihydro-1,3,4-oxadiazol-2-yl)propyl)-4-hydroxy-4-methylchroman-8-sulfonamide has an endothermic peak of about 154, 155, 156, 157, 158, 159, 160, 161, 162, 163, 164, 165, 166, 167, 168, 169, or 170° C. measured by DSC. In additional embodiments, the optical purity of this crystalline form is 100% ee.

In some embodiments, the disclosure relates to a crystalline form of N-((1S,2R)-2-(3-bromo-6-fluoro-2-methylphenyl)-1-(5-oxo-4,5-dihydro-1,3,4-oxadiazol-2-yl)propyl)-5-chloro-4-hydroxy-4-methylchroman-8-sulfonamide. In additional embodiments, the X-ray diffraction pattern of this crystalline form has two or more, three or more, four or more, five or more, six or more, seven or more, eight or more, or nine peaks at (2θ±0.2, 0.3, 0.4, 0.5, 0.6, 0.7, 0.8, 0.9 or 1.0°) of 6.8°, 7.8°, 11.2°, 13.4°, 13.7°, 16.0°, 17.1°, 17.8° and 23.2°. In further embodiments, the crystalline form of N-((1S,2R)-2-(3-bromo-6-fluoro-2-methylphenyl)-1-(5-oxo-4,5-dihydro-1,3,4-oxadiazol-2-yl)propyl)-5-chloro-4-hydroxy-4-methylchroman-8-sulfonamide has an endothermic peak from about 154, 155, 156, 157, 158, 159, 160, or 161° C. to about 160, 161, 162, 163, 164, 165, 166, 167, 168, 169 or 170° C. as measured by DSC. In some embodiments, the crystalline form of N-((1S,2R)-2-(3-bromo-6-fluoro-2-methylphenyl)-1-(5-oxo-4,5-dihydro-1,3,4-oxadiazol-2-yl) propyl)-5-chloro-4-hydroxy-4-methylchroman-8-sulfonamide has an endothermic peak from 155° C. to 168° C., from 158° C. to 162° C., from 159° C. to 161° C., from 159° C. to 165° C., or from 160° C. to 163° C. as measured by DSC. In additional embodiments, the crystalline form of N-((1S, 2R)-2-(3-bromo-6-fluoro-2-methylphenyl)-1-(5-oxo-4,5-dihydro-1,3,4-oxadiazol-2-yl)propyl)-5-chloro-4-hydroxy-4-methylchroman-8-sulfonamide has an endothermic peak of about 154, 155, 156, 157, 158, 159, 160, 161, 162, 163, 164, 165, 166, 167, 168, 169, or 170° C. measured by DSC. In additional embodiments, the optical purity of this crystalline form is 100% ee.

In some embodiments, the disclosure relates to a crystalline form of 5-chloro-N-((1S,2R)-2-(3-chloro-6-fluoro-2-methylphenyl)-1-(5-oxo-4,5-dihydro-1,3,4-oxadiazol-2-yl) propyl)-4-hydroxy-4-methyl-d3-chroman-8-sulfonamide. In additional embodiments, the X-ray diffraction pattern of this crystalline form has two or more, three or more, four or more, five or more, six or more, seven or more, eight or more, or nine peaks at (2θ±0.2, 0.3, 0.4, 0.5, 0.6, 0.7, 0.8, 0.9 or 1.0°) of 6.8°, 7.8°, 11.2°, 13.4°, 13.7°, 16.0°, 17.1°, 17.8° and 23.2°. In further embodiments, the crystalline form of 5-chloro-N-((1S,2R)-2-(3-chloro-6-fluoro-2-methylphenyl)-1-(5-oxo-4,5-dihydro-1,3,4-oxadiazol-2-yl)propyl)-4-hydroxy-4-methyl-d3-chroman-8-sulfonamide has an endothermic peak from 155° C. to 168° C., from 158° C. to 162° C., from 159° C. to 161° C., from 159° C. to 165° C., or from 160° C. to 163° C. as measured by DSC. In additional embodiments, the crystalline form of 5-chloro-N-((1S,2R)-2-(3-chloro-6-fluoro-2-methylphenyl)-1-(5-oxo-4,5-dihydro-1,3,4-oxadiazol-2-yl)propyl)-4-hydroxy-4-methyl-d3-chroman-8-sulfonamide has an endothermic peak of about 154, 155, 156, 157, 158, 159, 160, 161, 162, 163, 164, 165, 166, 167, 168, 169, or 170° C. measured by DSC. In additional embodiments, the optical purity of this crystalline form is 100% ee.

In some embodiments, the disclosure relates to a crystalline form of 5-chloro-N-((1S,2R)-2-(6-fluoro-2,3-dimethylphenyl)-1-(5-oxo-4,5-dihydro-1,3,4-oxadiazol-2-yl)propyl)-4-hydroxychroman-8-sulfonamide. In additional embodiments, the X-ray diffraction pattern of this crystalline form has two or more, three or more, four or more, five or more, six or more, seven or more, eight or more, or nine peaks at (2θ±0.2, 0.3, 0.4, 0.5, 0.6, 0.7, 0.8, 0.9 or 1.0°) of 6.8°, 7.8°, 11.2°, 13.4°, 13.7°, 16.0°, 17.1°, 17.8° and 23.2°. In further embodiments, the crystalline form of 5-chloro-N-((1S,2R)-2-(6-fluoro-2,3-dimethylphenyl)-1-(5-oxo-4,5-dihydro-1,3,4-oxadiazol-2-yl)propyl)-4-hydroxychroman-8-sulfonamide has an endothermic peak from about 154, 155, 156, 157, 158, 159, 160, or 161° C. to about 160, 161, 162, 163, 164, 165, 166, 167, 168, 169 or 170° C. as measured by DSC. In some embodiments, the crystalline form of 5-chloro-N-((1S,2R)-2-(6-fluoro-2,3-dimethylphenyl)-1-(5-oxo-4,5-dihydro-1,3,4-oxadiazol-2-yl)propyl)-4-hydroxychroman-8-sulfonamide has an endothermic peak from 155° C. to 168° C., from 158° C. to 162° C., from 159° C. to 161° C., from 159° C. to 165° C., or from 160° C. to 163° C. as measured by DSC. In additional embodiments, the crystalline form of 5-chloro-N-((1S,2R)-2-(6-fluoro-2,3-dimethylphenyl)-1-(5-oxo-4,5-dihydro-1,3,4-oxadiazol-2-yl)propyl)-4-hydroxychroman-8-sulfonamide has an endothermic peak of about 154, 155, 156, 157, 158, 159, 160, 161, 162, 163, 164, 165, 166, 167, 168, 169, or 170° C. measured by DSC. In additional embodiments, the optical purity of this crystalline form is 100% ee.

In some embodiments, the X-ray diffraction pattern of the crystalline form of the present disclosure has two or more peaks at (2θ±0.2°) of 6.8°, 7.8°, 11.2°, 13.4°, 13.7°, 16.0°, 17.1°, 17.8° and 23.2°. In some embodiments, the crystalline form has an endothermic peak from 155° C. to 168° C. as measured by DSC. In additional embodiments, the crystalline form of the present invention may be characterized by a combination of the embodiments described above that are not inconsistent with each other. For example, the crystalline form may be characterized by a combination of the above-described peaks of the X-ray diffraction pattern and the above-described endothermic peak measured by DSC.

The term "about" used for the peak temperature of the endothermic peak in the DSC curve means that temperature value within ±2, 3, 4 or 5° C. of the value.

Unless otherwise specified herein, the term "about" when used in connection with a numeric value or a range of values which is provided to characterize a particular solid form, e.g., a specific temperature or temperature range; a mass change, such as, e.g., a mass change as a function of temperature or humidity; a solvent or water content, in terms of, e.g., mass or a percentage; or a peak position, such as, e.g., in analysis by IR or Raman spectroscopy or XRPD; indicate that the value or range of values may deviate to an extent deemed reasonable to one of ordinary skill in the art while still describing the particular solid form. For example, in particular embodiments, the term "about" when used in this context and unless otherwise specified, indicate that the numeric value or range of values may vary within 25, 20, 15, 10, 9, 8, 7, 6, 5, 4, 3, 2, 1, 0.5, or 0.25% of the recited value or range of values.

In some embodiments, the crystalline form, co-crystal or benzoic acid salt disclosed herein may comprise a plurality of crystals (crystal polymorphs) having spatially regular atomic arrangements and different physicochemical properties may result. In additional embodiments, the crystalline form, co-crystal or benzoic acid salt described herein may be a mixture with the crystal polymorphs.

In some embodiments, in the crystalline form, co-crystal or benzoic acid salt of the present disclosure, the molar ratio of the sulfonamide compound to the benzoic acid is about 0.4 to about 1.6, about 0.6 to about 1.4, about 0.8 to about 1.2, about 0.9 to about 1.1, or about 1 to about 1. In additional embodiments, in the crystalline form, co-crystal or benzoic acid salt of the present disclosure, the molar ratio of the sulfonamide compound to the benzoic acid is from about 0.4, 0.5, 0.6, 0.7, 0.8, 0.9, 1, 1.1, 1.2, 1.3 to about 1.3, 1.2, 1.1, 1.0, 0.9, 0.8, 0.7, 0.6, 0.5, or 0.4. In further embodiments, the molar ratio of the sulfonamide compound and the benzoic acid is about 1:1.

In accordance with some embodiments of the crystalline forms, co-crystals or benzoic acid salts of the present disclosure, the sulfonamide compound or benzoic acid may be substituted with one or more radioactive isotopes or a non-radioactive isotope.

In some embodiments, the optical purity of the crystalline form, co-crystal or benzoic acid salt disclosed herein is at least about 70, 80, 85, 90, 91, 92, 93, 94, 95, 96, 97, 98, 99, 99.5 or 99.8%. As used herein, the optical purity or a chiral purity refers to the ratio of the observed optical rotation of a sample having a mixture of enantiomers to the optical rotation of one pure enantiomer. In additional embodiments, the optical purity is about 95% or more. In further embodiments, the optical purity is about 98% or more. In yet further embodiments, the optical purity is about 100%. In some embodiments, the optical purity may be measured by using HPLC. In some embodiments, the present disclosure relates to methods of increasing the optical purity of a sulfonamide compound disclosed herein by mixing the sulfonamide compound with benzoic acid or by forming a crystalline form, co-crystal or benzoic acid salt by the methods described herein.

In certain embodiments, the crystalline form, co-crystal or benzoic acid salt of a compound disclosed herein may be physically and/or chemically pure. In certain embodiments, the crystalline form, co-crystal or benzoic acid salt of a compound disclosed herein may be at least about 100, 99, 98, 97, 96, 95, 94, 93, 92, 91, 90, 89, 88, 87, 86, 85, 84, 83, 82, 81 or 80% physically and/or chemically pure. In some embodiments, the crystalline form, co-crystal or benzoic acid salt of a compound disclosed herein is substantially pure. As used herein and unless otherwise specified, a sample comprising a particular crystalline form or amorphous form that is "substantially pure," e.g., substantially free of other solid forms and/or of other chemical compounds, contains, in particular embodiments, less than about 25%, 20%, 15%, 10%, 9%, 8%, 7%, 6%, 5%, 4%, 3%, 2%, 1%, 0.75%, 0.5%, 0.25% or 0.1% percent by weight of one or more other solid forms and/or of other chemical compounds.

In some embodiments, the crystalline form, co-crystal or benzoic acid salt disclosed herein is stable upon exposure to conditions of about 30, 40, 50, 60, 70 or 80° C. and about 65, 70, 75, 80 or 85% relative humidity for about 1, 2, 3, 4, 5, 6, 7, 8, 12, 16, 24, 36, 48, 60, 72, 84, 96, 108, 120, 132, 144, or 156 weeks or more and for about 160, 156, 150, 138, 126, 114, 102, 90, 78, 66, 54, 42, 30, 24, 18, 12 or 6 weeks or less. The condition may be in a closed or open condition. As used herein, a "closed" condition may mean that a lid of a bottle containing the sample is closed or sealed during the stability experiment, and an "open" condition may mean that the lid is open. In additional embodiments, the crystalline form, co-crystal or benzoic acid salt disclosed herein is stable upon exposure to conditions of about 40° C. and about 75% relative humidity for at least about 1, 2, 3, 4, 5, 6, 7, 8, 9, 10, 11, 12, 13, 14, 15, 16, 17, 18, 19, 20, 21, or 22 weeks. In some embodiments, the condition is a closed condition. In further embodiments, the crystalline form, co-crystal or benzoic acid salt disclosed herein is stable upon exposure to conditions of about 40° C. and about 75% relative humidity for about 4 weeks. In some embodiments, the condition is a closed condition. Thus, the crystalline forms, co-crystals or benzoic acid salts disclosed herein exhibit excellent storage stability over an extended period. Herein, being "stable" means that (i) the change in the optical purity is about 1.0, 0.5, 0.3, 0.1, 0.05, or 0.01% or less compared to the initial optical purity, (ii) the increase in impurities is about 1.0, 0.5, 0.3, 0.1, 0.05, or 0.01% or less compared to the initial amount of impurities, and/or (iii) the X-ray diffraction pattern maintains 10, 20, 30, 40, 50, 60, 70, 80, or 90% or more of the initial peaks at (2θ±0.2°).

Another aspect of the present disclosure relates to a method of preparing the crystalline form, co-crystal and/or benzoic acid salt described herein, the method comprising: dissolving benzoic acid and the sulfonamide compound described herein in a solvent system comprising at least two solvents; and supersaturating the solvent system until the crystalline form, co-crystal and/or benzoic acid salt forms and is isolated from the solvent system. In another aspect, the present disclosure relates to a method of preparing a crystalline form of a sulfonamide compound disclosed herein from a non-crystalline form, the method comprising: dissolving the benzoic acid and the sulfonamide compound in a solvent system comprising at least two solvents; and supersaturating the solvent system until the product crystallizes from the solvent system.

In some embodiments, the method may further comprise adding or mixing the benzoic acid with a sulfonamide compound disclosed herein. In additional embodiments, from about 0.8, 0.9, 1, 2, 3, 4 or 5 to about 1, 2, 3, 4, 5, 6, 7, 8, or 9 molar equivalents of the benzoic acid compared to the sulfonamide compound may be mixed with the sulfonamide compound. In some embodiments, the method may further comprise adding or mixing from about 0.8 to about 5, from about 2 to about 5, from about 3 to about 5, from about 1 to from about 4, or from about 1 to 6 molar equivalent of benzoic acid with a sulfonamide compound disclosed herein. In additional embodiments, about 1, 2, 3, 4, 5, 6, or 7 molar equivalents of the benzoic acid compared to the sulfonamide compound may be mixed with the sulfonamide compound.

In additional embodiments, the dissolving step may comprise adding or mixing the solvent system with the benzoic acid and the sulfonamide compound, wherein the solvent system is in an amount of about 10 to about 40 times, from about 20 to about 30 times, or from about 10 to about 30 times in volume, including about 10, 11, 12, 13, 14, 15, 18, 20, 22, 25, 27, 30, 35, 38 or 40 times. In further embodiments, the dissolving step may comprise adding the solvent system with the benzoic acid and the sulfonamide compound, wherein the solvent system is in an amount of from about 10, 15, 20, 25, 30, 35, 40 to about 60, 55, 50, 45, 40, 35 or 30 times in volume. In additional embodiments, at least one of the at least two solvents in the solvent system is heptane or toluene. In further embodiments, the solvent system comprises heptane and toluene.

In further embodiments, in the solvent system or in the mixed solution of heptane and toluene, the toluene ratio is from about 5, 6, 7, 8, 9, 10 or 11 to about 10, 15, 17 or 20%, including about 5, 8, 10, 11, 12, 13, 14, 15, 16, 17, 18, 19 and 20%. In further embodiments, in the mixed solution of heptane and toluene, the toluene ratio is from 5 to 20%, from 10 to 20%, from 5 to 10%, or from 8 to 15%.

In some embodiments, the supersaturating step comprises heating the solvent system. In further embodiments, the supersaturating step comprises mixing the suspension from the dissolving step at a temperature above room temperature or from about 38, 39, 40, 41, 42, 43, 44, 45, 46, 47, 48, 49, 50, 51, 52, 53, 54, 55 or 56° C. to about 50, 55, 56, 57, 58, 59, 60, 61, 62, 63, 64, 65 or 66° C. for from about 1,2,3,4 or 5 hours to about 4, 5, 6, 7, 8, 9, 10, 15, 20, 30 or 40 hours. In yet further embodiments, the supersaturating step comprises mixing the suspension at a temperature from about 40 to about 60° C., from about 50 to about 60° C., from about 40 to about 50° C., or from about 38 to about 65° C. for from about 1 to about 40 hours, from about 3 to about 4 hours, from about 4 to about 5 hours, or about 3 to about 10 hours. In additional embodiments, the supersaturating step comprises mixing the suspension at a temperature from about 40 to about 60° C. for from about 3 to about 10 hours.

In some embodiments, the method of preparing the crystalline form, co-crystal and/or benzoic acid salt described herein further comprises washing the product obtained from the supersaturating step to remove the remaining excessive benzoic acid.

Although prodrugs of the crystalline forms, co-crystals or benzoic acid salts as described herein are also included in the present disclosure, the term "prodrug" refers to compounds which convert into a compound disclosed herein or a salt thereof by a reaction with an enzyme or gastric acid under physiological conditions in vivo, i.e., the compounds which convert into a compound of the present disclosure or a salt thereof by enzymatic oxidation, reduction, or hydrolysis and the like or compounds which convert into a compound disclosed herein or a salt thereof by action of gastric acid. Furthermore, a prodrug of a compound disclosed herein or a salt thereof may be a compound which converts into a compound disclosed herein or a salt thereof under physiological conditions such as described in Hirokawa Shoten 1990 annual "Development of Pharmaceuticals" Vol. 7, Molecular Design, pages 163-198.

Furthermore, the crystalline forms, co-crystals or benzoic acid salts of the present disclosure may be a solvate (e.g., hydrate, etc.) or a non-solvate, both of which are encompassed in the compound disclosed herein or a salt thereof. The compounds labeled with isotopes (e.g., deuterium, $^3$H, $^4$C, $^{35}$S, $^{125}$I etc.) and the like are also encompassed by the compounds disclosed herein or a salt thereof.

The crystalline form, co-crystal or benzoic acid salt described herein exhibits inhibitory activity against RNR. The crystalline form, co-crystal or benzoic acid salt as described herein is useful as a medicine for prevention or treatment of RNR-related diseases without causing side effects based on the off-target effects of the iron ions requiring protein due to its excellent RNR inhibitory activity and its structure and does not chelate to metal ions. The "RNR-related disease" includes diseases the incidence of which can be decreased or the symptoms of which are in remission or alleviated and/or completely cured by deleting or suppressing and/or inhibiting functions of RNR. Such diseases include, for example, malignant tumors. Malignant tumors of interest are not particularly limited, and may include head and neck cancers, gastrointestinal cancers (e.g., esophageal cancer, gastric cancer, duodenal cancer, liver cancer, biliary tract cancer (e.g., gallbladder or bile duct cancer, etc.), pancreatic cancer, colorectal cancer (e.g., colon cancer, rectal cancer etc.), etc.), lung cancer (e.g., non-small cell lung cancer, small cell lung cancer, mesothelioma, etc.), breast cancer, genital cancer (e.g., ovarian cancer, uterine cancer (e.g., cervical cancer, endometrial cancer, etc.), etc.), urinary cancer (e.g., kidney cancer, bladder cancer, prostate cancer, testicular tumor, etc.), hematopoietic tumors (e.g., leukemia, malignant lymphoma, multiple myeloma, etc.), bone and soft tissue tumors, skin cancer, brain tumors and the like.

"RNR" herein includes a human or non-human RNR, preferably a human RNR.

Accordingly, the present disclosure provides a RNR inhibitor which includes the crystalline form, co-crystal or benzoic acid salt described herein as an active ingredient. Furthermore, the present disclosure relates to the use of the crystalline form, co-crystal or salt described herein for the manufacture of the RNR inhibitors. The present disclosure also provides the use of the crystalline form, co-crystal or benzoic acid salt described herein as RNR inhibitors. Furthermore, the present disclosure provides the crystalline form, co-crystal or benzoic acid salt described herein for use in the prevention or treatment of disorders associated with RNR inhibitors.

In yet another embodiment, the present disclosure provides a medicine containing the crystalline form, co-crystal or benzoic acid salt described herein as an active ingredient. Furthermore, the present disclosure relates to the use of the crystalline form, co-crystal or benzoic acid salt described herein for the manufacture of a medicament. Further, the present disclosure provides the use as medicaments of the crystalline form, co-crystal or benzoic acid salt described herein. Further, the present disclosure provides the crystalline form, co-crystal or benzoic acid salt described herein for use as a medicament.

In yet another embodiment, the present disclosure provides a pharmaceutical composition comprising the crystalline form, co-crystal or benzoic acid salt described herein and a pharmaceutically acceptable carrier. The crystalline form, co-crystal or benzoic acid salt disclosed herein has low or no hygroscopicity and low chargeability, resulting in excellent handling properties. As the hygroscopicity is reduced, the problem of preservation and quality control of humidity present in the storage state is alleviated, and at the time of manufacturing a solid preparation, such as a tablet or a capsule, the quality of the preparation (uniformity) by mass control may be easily controlled. In addition, since the chargeability is low, adhesion to manufacturing equipment and packaging is not significant.

In some embodiments, the medicament or pharmaceutical composition is a therapeutic agent for RNR-related diseases, and in a more preferred embodiment, the medicament or pharmaceutical composition is an antitumor agent.

In additional embodiments, the present disclosure relates to administering an effective amount of the crystalline form, co-crystal or benzoic acid salt described herein to a subject in need thereof to provide a RNR activity suppression method. Further, the present disclosure comprises administering an effective amount of the crystalline form, co-crystal or salt described herein to the subject to provide a method of preventing, ameliorating, or treating RNR-related diseases.

In some embodiments, a method of preventing, ameliorating, or treating RNR-related diseases is a method of preventing, ameliorating, or treating tumors. In this method, the subjects include human or non-human animals (e.g., cows, pigs, horses, dogs, cats and the like) in need of such a method. In additional embodiments, the subject may be a subject suffering from an RNR-related disease described herein.

When using the crystalline form, co-crystal or benzoic acid salt described herein as a pharmaceutical, it is optionally formulated with a pharmaceutically acceptable carrier, and can be adopted various dosage forms depending on the prevention or therapeutic purposes, and as the dosage forms include, for example, oral agents, injections, suppositories, ointments, and any of such patches. Since the crystalline form, co-crystal or benzoic acid salt described herein has excellent oral absorbability, oral agents are preferable. These dosage forms can be prepared by conventional methods commonly known in the art.

With respect to pharmaceutically acceptable carriers, conventional various organic or inorganic carrier substances are used as pharmaceutical materials, formulated as: excipients, binders, disintegrating agents, lubricants, coloring agents for solid preparations; and solvents, solubilizing agents, suspending agents, isotonizing agents, buffers, soothing agent for liquid preparations and the like. Further, if necessary, pharmaceutical additives can also be used, which include preservative agents, antioxidants, coloring agents, sweetening agents, flavoring agents, and stabilizing agents.

With respect to pharmaceutically acceptable carriers and the pharmaceutical additives, in general, they include, for example, as the excipient: lactose, sucrose, sodium chloride, glucose, starch, calcium carbonate, kaolin, microcrystalline cellulose, silicic acid and the like; as binders:water, ethanol, propanol, simple syrup, glucose solution, starch solution, gelatin solution, carboxymethyl cellulose, hydroxypropyl cellulose, hydroxypropyl starch, methyl cellulose, ethyl cellulose, include shellac, calcium phosphate, polyvinylpyrrolidone, and the like; as disintegrants: dry starch, sodium alginate, agar powder, sodium hydrogen carbonate, calcium carbonate, sodium lauryl sulfate, stearic acid monoglyceride, lactose and the like; as lubricants: purified talc stearate, borax, polyethylene glycol and the like; as colorants: titanium oxide, iron oxide and the like; as flavoring agents: sucrose, orange peel, citric acid, and tartaric acid and the like.

An oral solid preparation can be prepared by adding an excipient to the crystalline form, co-crystal or benzoic acid salt described herein, and if necessary, binders, disintegrants, lubricants, colorants, or flavoring agents and the like can be further added, followed by formulating into tablets, coated tablets, granules, powders, capsules and the like.

Injectable forms can be prepared by adding pH control agents, buffers, stabilizers, isotonic agents, local anesthetic agents and the like to the crystalline form, co-crystal or benzoic acid salt described herein, followed by formulating into subcutaneous, intramuscular and intravenous injections in a conventional manner.

When preparing a rectal suppository, a suppository can be manufactured by a conventional method after adding an excipient and, if necessary, a surfactant and the like to the active ingredient described herein. When preparing in the form of an ointment, for example, paste, cream and gel, the base, stabilizer, wetting agent, preservative and the like are blended as necessary and formulated by a conventional method. For example, white petrolatum, paraffin, glycerin, cellulose derivatives, polyethylene glycol, silicon, bentonite and the like may be used as the base. As preservatives, methyl parahydroxybenzoate, ethyl parahydroxybenzoate, propyl parahydroxybenzoate and the like may be used. In the case of preparing a patch, the ointment, cream, gel, paste or the like may be applied to a support by a known method. As the support, a woven fabric made of cotton, spun, chemical fiber, a nonwoven fabric, a film of soft vinyl chloride, polyethylene, polyurethane or the like or a foam sheet may be suitable.

The amount of the crystalline form, co-crystal or benzoic acid salt described herein to be formulated in each dosage unit forms described above can be, in general, per dosage unit form, from about 0.05, 0.1, 1, 5, 10 or 20 to about 100, 500 or 1000 mg for an oral dosage, from about 0.01 or 0.1 to about 200, 300 or 500 mg for injection, and from about 1, 5 or 10 to about 100, 500 or 1000 mg for suppositories with the proviso that these amounts may be altered depending on the symptoms of the patients to be applied or its dosage forms.

Further, the daily dose of a drug with the dosage form is, with respect to the crystalline form, co-crystal or salt described herein, 0.05 to 5000 mg per day for adult (body weight 50 kg), preferably 0.1 to 2000 mg, and preferably the aforementioned amount is administered once or 2 to 3 times a day with the proviso that they may be altered depending on symptoms of the patients, weight, age, or gender and the like.

The analogous substances described in FIGS. 10 to 12 are also included in the present application. The analogous substances of the present invention may be synthesized by known methods or may be obtained from commercially available products. The analogous substances can be identified by comparing the retention times in high-performance liquid chromatography, mass spectra, and results from a photodiode array (PDA) between the thus-obtained analogous substances and the analogous substances detected in accordance with the present invention.

Further, these analogous substances can be quantitatively measured by either an external standard method or internal standard method.

When these analogous substances are possibly contained as impurities in a medicinal drug or pharmaceutical preparation, these analogous substances are regulated in accordance with guideline ICH-Q3A of the International Council for Harmonization of Technical Requirements for Pharmaceuticals for Human Use. The method of the present invention is very useful since it is possible to confirm whether the standard of the guideline is satisfied.

The analogous substances are shown in the following table.

TABLE 1

| Name | Chemical Structure |
|---|---|
| OPC: (2S,3R)-2-((2-carbamoyl-4-chlorophenyl)sulfonamido)-3-(6-fluoro-2,3-dimethylphenyl)butanoic acid | 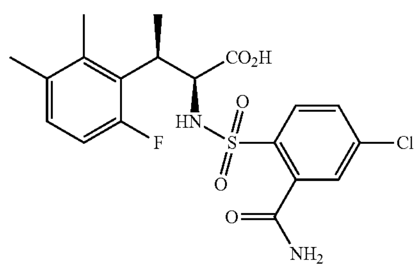 [SMILES: Cc1ccc(F)c([C@@H](C)[C@H](NS(=O)(=O)c2ccc(Cl)cc2C(N)=O)C(=O)O)c1C] |
| SAC: 5-((1S,2R)-1-(5-chloro-1,1-dioxido-3-oxobenzo[d]isothiazol-2(3H)-yl)-2-(6-fluoro-2,3-dimethylphenyl)propyl)-1,3,4-oxadiazol-2(3H)-one | 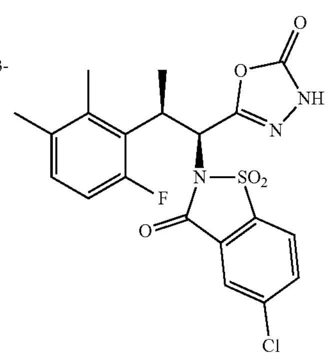 |
| OPH: 5-chloro-2-(N-((2S,3R)-3-(6-fluoro-2,3-dimethylphenyl)-1-hydrazinyl-1-oxobutan-2-yl)sulfamoyl)benzamide | 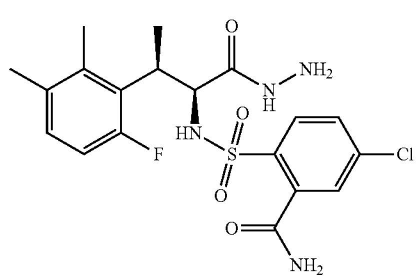 [SMILES: Cc1ccc(F)c([C@@H](C)[C@H](NS(=O)(=O)c2ccc(Cl)cc2C(N)=O)C(=O)NN)c1C] |

TABLE 1-continued

| Name | Chemical Structure |
|---|---|
| deMe: 5-chloro-2-(N-((1S,2R)-2-(2-fluoro-5-methylphenyl)-1-(5-oxo-4,5-dihydro-1,3,4-oxadiazol-2-yl)propyl)sulfamoyl)benzamide | 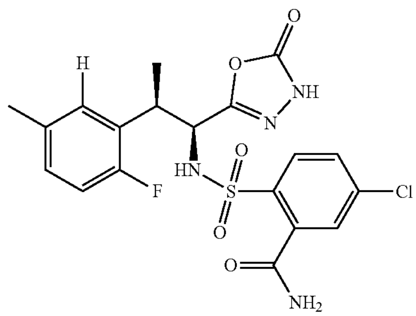 [SMILES: Cc1ccc(F)c([C@@H](C)[C@H](NS(=O)(=O)c2ccc(Cl)cc2C(N)=O)c2n[nH]c(=O)o2)c1] |
| OPD1 | 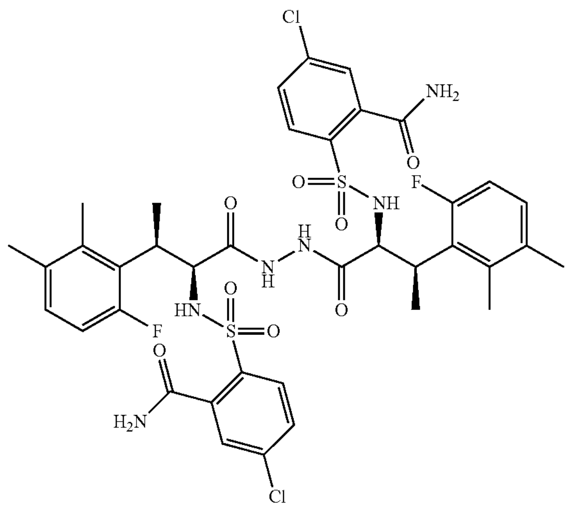 |
| OPHD | 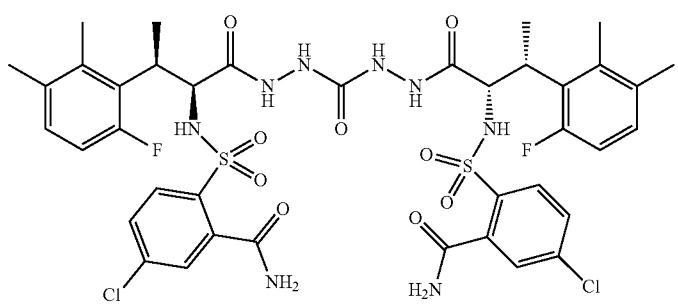 |

EXAMPLES

The present invention according to some embodiments is described below in more detail with experimental examples but the present invention is not intended to be limited to these examples.

Various reagents used in the examples were commercially available products, unless otherwise stated. Biotage Ltd. SNAP-ULTRA (registered trademark) Silica prepacked column was used for a silica gel column chromatography, or Biotage made SNAP KP-C18-HS (registered trademark) Silica prepacked column was used for a reverse phase silica gel column chromatography. HPLC purified by preparative reverse phase column chromatography was performed under the following conditions. Injection volume and gradient was carried out appropriately.

Column: YMC-Actus Triart C18, 30×50 mm, 5 μm
UV detection: 254 nm
Column flow rate: 40 mL/min
Mobile phase: water/acetonitrile (0.1% formic acid)
Injection amount: 1.0 mL
Gradient: water/acetonitrile (10% to 90%)

AL400 (400 MHz; JEOL (JEOL)) and Mercury400 (400 MHz; Agilent Technologies) were used for NMR spectra, and tetramethylsilane was used as an internal standard when tetramethylsilane was included in the heavy solvent, otherwise it was measured using NMR solvent as an internal standard, showing all δ value in ppm. Furthermore, LCMS spectra were measured under the following conditions using a Waters made ACQUITY SQD (quadrupole).

Column: Waters made ACQUITY UPLC (registered trademark) BEH C18, 2.1×50 mm, 1.7 μm
MS detection: ESI negative
UV detection: 254 and 280 nm Column flow rate: 0.5 mL/min
Mobile phase: water/acetonitrile (0.1% formic acid)
Injection amount: 1 μL

TABLE 2

| | Gradient | |
|---|---|---|
| Time (min) | Water | Acetonitrile |
| 0 | 95 | 5 |
| 0.1 | 95 | 5 |
| 2.1 | 5 | 95 |
| 3.0 | STOP | |

The meanings of the abbreviations are shown below.
s: singlet
d: doublet
t: triplet
q: quartet
dd: double doublet
dt: double triplet
td: triple doublet
tt: triple triplet
ddd: double double doublet
ddt: double double triplet
dtd: double triple doublet
tdd: triple-double doublet
m: multiplet
br: broad
brs: broad singlet
DMSO-$d_6$: deuterated dimethyl sulfoxide
CDCl$_3$: heavy chloroform
CD$_3$OD: heavy methanol
CDI: 1,1'-carboxymethyl sulfonyl diimidazole
DAST: N,N-diethylaminosulfur trifluoride
DIBAL-H: diisobutylaluminum hydride
DMF: dimethylformamide
DMSO: dimethylsulfoxide
THF: Tetrahydrofuran
  WSC=EDCI=1-ethyl-3-(3-dimethylaminopropyl)carbodiimide
  HOBt=1-hydroxybenzotriazole Reference Example A1:
2-(1-bromoethyl)-1-fluoro-3,4-dimethylbenzene

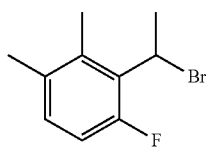

[Formula I]

(Step 1) 1-(6-fluoro-2,3-dimethylphenyl) Ethanol

After dropping a diethyl ether solution of methylmagnesium bromide (3.0 M, 70 mL) to a THF solution of 6-fluoro-2,3-dimethyl-benzaldehyde (22.0 g) (300 mL) at 0° C., the reaction mixture was stirred at room temperature for 1 hour. Under ice-bath condition, a saturated aqueous ammonium chloride solution (150 mL) was added dropwise, and ethyl acetate (200 mL) was added, and the resultant was separated into different layers. The organic layer was successively washed with HCl (1M, 200 mL), water (200 mL) and brine (200 mL), and then dried over anhydrous magnesium sulfate, and concentrated under reduced pressure to obtain 1-(6-fluoro-2,3 dimethylphenyl)ethanol (23.7 g).

(Step 2) Phosphorus tribromide (26.5 mL) was added dropwise at 0° C. to a chloroform solution (120 mL) of 1-(6-fluoro-2,3-dimethylphenyl)ethanol (23.7 g) obtained in the above Step 1, and the reaction solution was stirred for 30 minutes at 0° C. The reaction mixture was added to an ice-cold saturated aqueous sodium hydrogen carbonate (1L). After chloroform (500 mL) was added to the mixture, the resultant was separated into different layers, and the organic layer was successively washed with water (200 mL) and brine (200 mL). The organic layer was dried over anhydrous magnesium sulfate to give the title compound (29.5 g) by concentrating under reduced pressure.

Reference Example A2 and A3

Aldehyde and methylmagnesium bromide were reacted together as a starting material in the same manner as in Reference Example A1, Step 1 and Step 2, and then the resultant was reacted with phosphorus tribromide to obtain the compound of Reference Example A2 and A3 shown below.

TABLE 3

| Reference Example | Starting Material | Synthesized Compound |
|---|---|---|
| A2 | ![](CHO structure with Cl, F, methyl) | ![](Br structure with Cl, F, methyl) |
| A3 | ![](CHO structure with Br, F, methyl) | ![](Br structure with Br, F, methyl) |

Reference Example A4:
2-(1-bromoethyl)-4-ethyl-1-fluoro-3-methylbenzene

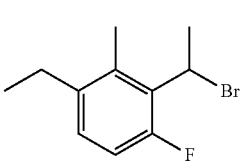

[Formula II]

(Step 1) 2-bromo-3-ethyl-6-fluorobenzaldehyde

To a THF solution (150 mL) of 2-bromo-1-ethyl-4-fluorobenzene (14.4 g), a THF solution of lithium diisopropylamide (1.5 M, 54 mL) was added dropwise at −78° C. After stirring the reaction solution for 30 minutes, DMF (6.5 mL) was added and the mixture was further stirred for 20 minutes. Water (50 mL) and hydrochloric acid (6 M, 50 mL) were successively added dropwise to the reaction solution, and the mixture was extracted twice with hexane (100 mL).

The combined organic layer was washed with brine (50 mL) twice, dried over anhydrous sodium sulfate, and concentrated under reduced pressure, and 2-bromo-3-ethyl-6-fluorobenzaldehyde (14.5 g) was obtained.

(Step 2) 3-ethyl-6-fluoro-2-methylbenzaldehyde

To a 1,4-dioxane solution (200 mL) of 2-bromo-3-ethyl-6-fluorobenzaldehyde obtained from Step 1 above (14.5 g), water (90 mL), tripotassium phosphate (32.0 g), methylboronic acid (6.4 g) and [bis (diphenylphosphino) ferrocene] palladium (II) dichloride dichloromethane additive (1.75 g) were added, and the reaction solution was heated under reflux at 110° C. for 2 hours. The reaction solution was allowed to cool to room temperature, and the mixture was further stirred for 2 hours after hexane (90 mL) was added. The reaction solution was filtered through CELITE, and the filtrate was separated after the residue was washed with hexane. The organic layer was washed twice with brine (100 mL), and after being dried over anhydrous sodium sulfate, it was concentrated under reduced pressure. The residue was purified by silica gel column chromatography (eluent: hexane/ethyl acetate), and 3-ethyl-6-fluoro-2-methylbenzaldehyde (8.4 g) was obtained.

(Step 3) According to the methods of Reference Example A1 Steps 1 and 2, using 3-ethyl-6-fluoro-2-methylbenzaldehyde (8.4 g) obtained in the above Step 2, the same operation was carried out to obtain the compound of Reference Example A4.

Reference Example B1: (2S,3R)-2-amino-3-(6-fluoro-2,3-dimethylphenyl) Butanoic Acid

[Formula III]

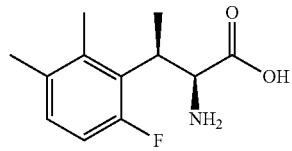

A DMF solution (50 mL) of 2-(1-bromoethyl)-1-fluoro-3,4-dimethylbenzene (14.0 g) obtained in Reference Example A1 was added dropwise to a DMF solution (50 mL) of (S)-2-[o-[(N-benzylprolyl)amino]phenyl]-benzylideneamino-acetate (2-)-N,N,N-nickel (II) (14.5 g), and potassium hydroxide (16.3 g), and the mixture was stirred at the same temperature for 1 hour. A saturated ammonium chloride solution (50 mL) and ethyl acetate (50 mL) were added to the reaction solution, the layers were separated, and the aqueous layer was extracted twice with ethyl acetate (50 mL). The combined organic layers were washed successively with water (50 mL) and brine (50 mL), dried over anhydrous sodium sulfate, and concentrated under reduced pressure. The residue was purified by silica gel column chromatography (eluent: ethyl acetate/hexane). The obtained compound was dissolved in methanol (120 mL), hydrochloric acid (3 M, 90 mL) was added, and the mixture was stirred at 80° C. for 45 minutes. Methanol was distilled off under reduced pressure, and chloroform (50 mL) and water (50 mL) were added to the residue. The aqueous layer was washed with chloroform (50 m L) and concentrated under reduced pressure. The residue was purified by reverse phase silica gel column chromatography (methanol/water) to give the title compound (2.0 g). H NMR (CD$_3$OD) δ: 7.03 (dd, J=8.2, 5.7 Hz, 1H), 6.79 (dd, J=11.7, 8.4 Hz, 1H), 3.74-3.87 (m, 2H), 2.29 (s, 3H), 2.25 (s, 3H), 1.40 (dd, J=6.8, 2.4 Hz, 3H)

Reference Examples B2-B4

After the alkylating agent obtained in Reference Examples A2-A4 and (S)-2-[o-[(N-benzylprolyl)amino]phenyl]-benzylideneamino-acetate (2-)-N, N, N-nickel (II) were reacted, the compounds of Reference Examples B2-B4 shown below were prepared by acid hydrolysis.

TABLE 4

| Reference Example | Starting Material (Reference example number or structural formula) | Synthesized Compound |
|---|---|---|
| B2 | A2 | ![structure with Cl and F]  |
| B3 | A3 | ![structure with Br and F] |
| B4 | A4 | ![structure with ethyl and F] |

Reference Example C1: 5-chloro-8-(chlorosulfonyl)-4-methyl-d 3-chroman-4-yl Acetate

[Formula IV]

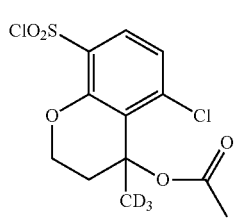

(Step 1) 8-bromo-5-chloro-4-methylchroman-4-ol

THF (50 mL) was added to diethyl ethyl ether solution (1.0 M, 63 mL) of methyl iodide-d3-magnesium, and THF solution (50 mL) of 8-bromo-5-chlorochroman-4-one (7.5 g) was added dropwise at room temperature. The reaction solution was stirred for 10 minutes at the same temperature and the layer was separated. In ice bath, hydrochloric acid (1 M, 50 mL) was slowly added dropwise, and ethyl acetate (50 mL) was added to separate layers. The aqueous layer was extracted with ethyl acetate (50 mL), and the combined organic layer was washed with brine (50 mL), dried over anhydrous sodium sulfate, and concentrated under reduced pressure. The residue was purified by silica gel column chromatography (eluent: hexane/ethyl acetate) to obtain 8-bromo-5-chloro-4-methylchroman-4-ol (7.7 g).

(Step 2) 8-bromo-5-chloro-4-methyl-d3-chroman-4-yl Acetate

To anhydrous acetic acid solution (100 mL) of 8-bromo-5-chloro-4-methylchroman-4-ol (7.7 g) obtained in the above Step 1, acetonitrile solution (12 mL) of scandium trifluoromethanesulfonate (III) (340 mg) was added dropwise at −40° C., and the reaction was stirred for 30 minutes at the same temperature. A saturated aqueous sodium hydrogen carbonate solution (100 mL) and ethyl acetate (100 mL) were sequentially added to the reaction solution, and the layers were separated. The aqueous layer was extracted with ethyl acetate (100 mL), and the combined organic layers were washed twice with saturated aqueous sodium hydrogen carbonate solution (100 mL) and once with brine (100 mL). The organic layer was dried over anhydrous sodium sulfate and concentrated under reduced pressure. The residue was purified by silica gel column chromatography (eluent: hexane/ethyl acetate) to obtain 8-bromo-5-chloro-4-methyl-d3-chroman-4-yl acetate (8.9 g).

(Step 3) 8-(benzylthio)-5-chloro-4-methyl-d3-chroman-4-yl Acetate

To 1,4-dioxane solution (70 mL) of 8-bromo-5-chloro-4-methyl-d3-chroman-4-yl acetate (6.7 g) obtained in the above Step 2, 4,5-bis(diphenylphosphino)-9,9-dimethylxanthene (600 mg), tris(dibenzylideneacetone) dipalladium (0) (480 mg), N, N-diisopropylethylamine (7.2 mL) and benzylmercaptan (2.8 ml) were added, and the reaction solution was stirred for 2 hours at 90° C. The reaction solution was allowed to cool to room temperature and filtered through CELITE. After washing the residue with hexane (50 mL), water (50 mL) was added to the filtrate and the layer was separated. The organic layer was washed with brine (50 mL), dried over anhydrous sodium sulfate, and concentrated under reduced pressure. The reaction solution was concentrated under reduced pressure, and the residue was purified by silica gel column chromatography (eluent: hexane/ethyl acetate) to obtain 8-(Benzylthio)-5-chloro-4-methyl-d3-chroman-4-yl acetate (6.3 g).

(Step 4) To acetonitrile solution (100 mL) of 8-(benzylthio)-5-chloro-4-methyl-d3-chroman-4-yl acetate (6.3 g) obtained in the above Step 3, water (3 mL), acetic acid (4.3 mL) and 1,3-dichloro-5,5-dimethylhydantoin (7.2 g) were each added at 0° C., and the reaction solution was stirred for 30 minutes at the same temperature. A saturated aqueous sodium hydrogen carbonate solution (70 mL) and ethyl acetate (70 mL) were added to the reaction solution, and the layers were separated. The aqueous layer was extracted with ethyl acetate (70 mL). The combined organic layers were washed with brine (70 mL), dried over anhydrous sodium sulfate, and concentrated under reduced pressure. The residue was purified by silica gel column chromatography (eluent: hexane/ethyl acetate) to obtain the title compound (5.3 g).

Reference Examples C2-C4

According to the method of Reference Example C1 Steps 1-4, the compounds of Reference Example C2 was synthesized with the starting materials listed in the following table. According to the method of Reference Examples C1 Steps 3 and 4, the compounds of Reference Examples C3 and C4 were synthesized.

TABLE 5

| Reference Example | Starting Material | Synthesized Compound |
|---|---|---|
| C2 | Br, Cl chromanone | ClO₂S, Cl chroman-4-yl acetate |
| C3 | Br, F chromanone | ClO₂S, F chromanone |
| C4 | Br, Cl chromanone | ClO₂S, Cl chromanone |

Reference Example D1: 5-((1S,2R)-1-Amino-2-(6-fluoro-2,3-dimethylphenyl)propyl)-1,3,4-oxadiazol-2(3H)-one Monohydrochloride

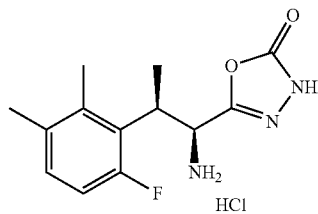

[Formula V]

(Step 1) (2S,3R)-2-((tert-butoxycarbonyl)amino)-3-(6-fluoro-2,3-dimethylphenyl)butanoic Acid Water (9 mL), 1,4-dioxane (9 mL) and triethylamine (955 μL) were sequentially added to (2S,3R)-2-amino-3-(6-fluoro-2,3-dimethylphenyl)butanoic acid (515 mg) obtained in Reference Example B1, and the mixture was cooled to 0° C. Di-tert-butyl dicarbonate (650 mg) was added to the reaction solution at the same temperature, and the mixture was stirred for 45 minutes. The reaction solution was added to hydrochloric acid (1 M, 20 mL) and extracted with ethyl acetate (20 mL). The organic layer was washed with brine (20 mL), dried over anhydrous magnesium sulfate, and concentrated under reduced pressure. The residue is purified by silica gel column chromatography (eluent: hexane/ethyl acetate/2% acetic acid) to obtain (2S,3R)-2-((tert-butoxy-carbonyl)amino)-3-(6-fluoro-2,3-dimethylphenyl)butanoic acid (745 mg).

(Step 2) tert-butyl ((1S,2R)-2-(6-fluoro-2,3-dimethylphenyl)-1-(5-oxo-4,5-dihydro-1,3,4-oxadiazol-2-yl)propyl)carbamate To a THF solution (14.0 mL) of (2S,3R)-2-(tert-butoxycarbonylamino)-3-(6-fluoro-2,3-dimethylphenyl)butanoic acid (440 mg) obtained in the above Step 1, CDI (302 mg) was added, and the reaction solution was stirred at room temperature for 20 minutes. The reaction solution was cooled to 0° C., hydrazine—monohydrate (200 µL) was added, and the mixture was stirred at the same temperature for 30 minutes. The reaction solution was added to water (20 mL) and extracted with ethyl acetate (20 mL). The organic layer was washed with brine (20 mL), dried over anhydrous sodium sulfate, and concentrated under reduced pressure. CDI (560 mg) was added to a 1,4-dioxane (14 mL) solution of the obtained residue, and the reaction solution was stirred at room temperature for 30 minutes. The reaction solution was added to water (20 mL) and extracted with ethyl acetate (20 mL). The organic layer was washed with brine (20 mL), dried over anhydrous sodium sulfate, and concentrated under reduced pressure. The obtained residue was purified by silica gel column chromatography by purification (eluent: hexane/ethyl acetate) to obtain tert-butyl ((1S,2R)-2-(6-fluoro-2,3-dimethylphenyl)-1-(5-oxo-4,5-dihydro-1,3,4-oxadiazol-2-yl)propyl)carbamate (356 mg).

(Step 3) tert-butyl ((1S,2R)-2-(6-fluoro-2,3-dimethylphenyl)-1-(5-oxo-4,5-dihydro-1,3,4-oxadiazol-2-yl)propyl)carbamate (550 mg) obtained in the above Step 2 was dissolved in hydrochloric acid-1,4-dioxane (4 M, 5.0 mL), and the reaction solution was stirred at room temperature for 1.5 hours. The reaction solution was concentrated under reduced pressure to obtain the title compound.

Reference Example D2 and D3

According to the method of Reference Example D1 Steps 1 to 3, the following compounds of Reference Examples D2 and D3 were synthesized.

Example 1: 5-bromo-2-(N-((1S, 2R)-2-(6-fluoro-2,3-dimethylphenyl)-1-(5-oxo-4,5-dihydro-1,3,4-oxadiazol-2-yl)propyl) sulfamoyl) Benzamide (Step 1) To 1,4-dioxane (5.0 mL) solution and water (5.0 mL) of (2S,3R)-2-amino-3-(6-fluoro-2,3-dimethylphenyl) butanoic acid (300 mg) obtained in Reference Example B1, triethylamine (570 µL) was added and then cooled to 0° C. 4-Bromo-2-cyanobenzene-1-sulfonyl chloride (362 mg) was added to the reaction solution, and the mixture was stirred at the same temperature for 45 minutes. The reaction solution was added to hydrochloric acid (1 M, 15 mL) and extracted with ethyl acetate (15 mL). The organic layer was washed with brine (20 mL), dried over anhydrous magnesium sulfate, and concentrated under reduced pressure. The residue was purified by silica gel column chromatography (eluent: hexane/ethyl acetate/2% acetic acid) to obtain (2S,3R)-2-(4-bromo-2-cyanophenylsulfonamido)-3-(6-fluoro-2,3-dimethylphenyl) butanoic acid (465 mg).

(Step 2) To a THF (5.0 mL) solution of (2S,3R)-2-(4-bromo-2-cyanophenylsulfonamido)-3-(6-fluoro-2,3-dimethylphenyl)butanoic acid (465 mg) obtained in the above Step 1, CDI (210 mg) was added, and the reaction solution was stirred at room temperature for 20 minutes. The reaction solution was cooled to 0° C., hydrazine • monohydrate (200 µL) was added, and the mixture was stirred at the same temperature for 20 minutes. The reaction solution was added to water (20 mL) and extracted with ethyl acetate (20 mL). The organic layer was washed with brine (20 mL), dried over anhydrous sodium sulfate, and concentrated under reduced pressure. CDI (211 mg) was added to a 1,4-dioxane (4.0 mL) solution of the obtained residue, and the reaction solution was stirred at 45° C. for 1 hour. The reaction solution was added to water (20 mL) and extracted with ethyl acetate (20 mL). The organic layer was washed with brine (20 mL), dried over anhydrous sodium sulfate, and concentrated under reduced pressure. The obtained residue was purified by silica gel column chromatography (eluent: hexane/ethyl acetate) to obtain 4-bromo-2-cyano-N-((1S, 2R)-2-(6-fluoro-2,3-dimethylphenyl)-1-(5-oxo-4,5-dihydro-1,3,4-oxadiazol-2-yl)propyl)benzenesulfonamide (386 mg).

TABLE 6

| Reference Example | Starting Material (Reference example number or structural formula) | Synthesized Compound |
|---|---|---|
| D2 | Reference Example B2 | 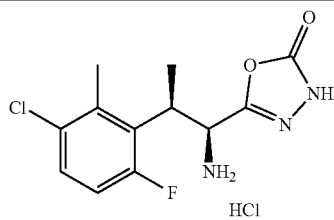 |
| D3 | Reference Example B3 | 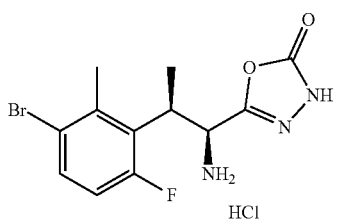 [SMILES: Cc1c(Cl)ccc(F)c1[C@@H](C)[C@H](N)c1n[nH]c(=O)o1 ; Cl] |

(Step 3) To a DMSO (5.0 mL) solution of 4-bromo-2-cyano-N-((1S,2R)-2-(6-fluoro-2,3-dimethylphenyl)-1-(5-oxo-4,5-dihydro-1,3,4-oxadiazol-2-yl)propyl)benzenesulfonamide (386 mg) obtained in the above Step 2, hydrogen peroxide water (1.0 mL) and potassium carbonate (420 mg) were added sequentially in an ice bath, and the reaction solution was stirred at 60° C. for 2.5 hours. The reaction solution was slowly added to hydrochloric acid (1 M, 15 mL) in an ice bath and then extracted with ethyl acetate (15 mL). The organic layer was washed with brine (20 mL), dried over anhydrous sodium sulfate, and concentrated under reduced pressure. The residue was purified by silica gel column chromatography (eluent: hexane/ethyl acetate) to give the title compound.

Examples 2-4

Compounds of Examples 2 to 4 were synthesized according to the method of Example 1, Steps 1 to 3. The necessary raw materials are listed in the following table.

TABLE 7

| Example | Starting Material | ArSO2Cl | Name of the Synthesized Compound |
| --- | --- | --- | --- |
| 2 | Reference Example B1 | ClO₂S—(benzene with NC and Cl substituents) | 5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide |
| 3 | Reference Example B4 | ClO₂S—(benzene with NC and Cl substituents) | 5-chloro-2-(N-((1S,2R)-2-(3-ethyl-6-fluoro-2-methylphenyl)-1-(5-oxo-4,5-dihydro-1,3,4-oxadiazol-2-yl)propyl)sulfamoyl)benzamide |
| 4 | Reference Example B2 | ClO₂S—(benzene with NC and Cl substituents) | 5-chloro-2-(N-((1S,2R)-2-(3-chloro-6-fluoro-2-methylphenyl)-1-(5-oxo-4,5-dihydro-1,3,4-oxadiazol-2-yl)propyl)sulfamoyl)benzamide |

Example 5: 5-chloro-N-((1S,2R)-2-(6-fluoro-2,3-dimethylphenyl)-1-(5-oxo-4,5-dihydro-1,3,4-oxadiazol-2-yl)propyl)-4-hydroxy-4-methyl-d3-chroman-8-sulfonamide Isomer A and Isomer B (Step 1) 5-chloro-8-(N-((1S,2R)-2-(6-fluoro-2,3-dimethylphenyl)-1-(5-oxo-4,5-dihydro-1,3,4-oxadiazol-2-yl)propyl)sulfamoyl)-4-methyl-d3-chroman-4-yl acetate To a pyridine (1.5 mL) solution of 5-((1S,2R)-1-amino-2-(6-fluoro-2,3-dimethylphenyl)propyl)-1,3,4-oxadiazol-2(3H)-one monohydrochloride (45 mg) obtained from Reference Example D1, 5-chloro-8-(chlorosulfonyl)-4-methyl-d3-chroman-4-ylacetate (80 mg) obtained in Reference Example C1 was added, and the reaction solution was stirred at room temperature for 12 hours. The reaction solution was concentrated under reduced pressure, and the obtained residue was purified by silica gel column chromatography (eluent: hexane/ethyl acetate) to obtain the title compound (59 mg) as a 1:1 diastereomer mixture.

(Step 2) A 1:1 diastereomer mixture of 5-chloro-8-(N-((1S,2R)-2-(6-fluoro-2,3-dimethylphenyl)-1-(5-oxo-4,5-dihydro-1,3,4-oxadiazol-2-yl)propyl)sulfamoyl)-4-methyl-d3-chroman-4-yl acetate (59 mg) obtained from Step 1 above was dissolved in methanol (2.0 mL) and water (1.0 mL), lithium hydroxide (5 mg) was added, and the reaction solution was stirred at 55° C. for 1 hour. After concentrating the reaction solution, hydrochloric acid (1 M, 10 mL) and ethyl acetate (10 mL) were added to the residue, and the layers were separated. The aqueous layer was extracted with ethyl acetate (10 mL), and the combined organic layers were washed with brine (10 mL). The organic layer was dried over anhydrous sodium sulfate and concentrated under reduced pressure. The residue was purified by reverse phase HPLC (water/acetonitrile), and the fractions were concentrated to give each of two diastereomeric products. The substance eluted first was designated Compound A, and the substance eluted later was designated as Compound B.

Examples 6-8

According to the method of Example 5 Step 2, the following compounds of Examples 6-8 were synthesized. In the case of separating the diastereomers, the previously eluted compound was designated as A and the later eluted compound as B. The ratio of diastereomers is 1:1 mixture unless otherwise specified. The necessary raw materials are listed in the following table.

TABLE 8

| Example | Starting Material | ArSO₂Cl | Name of the Synthesized Compound |
| --- | --- | --- | --- |
| 6A and 6B | Reference Example D2 | Reference Example C2 | 5-chloro-N-((1S,2R)-2-(3-chloro-6-fluoro-2-methylphenyl)-1-(5-oxo-4,5-dihydro-1,3,4-oxadiazol-2-yl)propyl)-4-hydroxy-4-methylchroman-8-sulfonamide |
| 7A and 7B | Reference Example D3 | Reference Example C2 | N-((1S,2R)-2-(3-bromo-6-fluoro-2-methylphenyl)-1-(5-oxo-4,5-dihydro-1,3,4-oxadiazol-2-yl)propyl)-5-chloro-4-hydroxy-4-methylchroman-8-sulfonamide |
| 8A and 8B | Reference Example D2 | Reference Example C1 | 5-chloro-N-((1S,2R)-2-(3-chloro-6-fluoro-2-methylphenyl)-1-(5-oxo-4,5-dihydro-1,3,4-oxadiazol-2-yl)propyl)-4-hydroxy-4-methyl-d3-chroman-8-sulfonamide |

Example 9: 5-fluoro-N-((1S,2R)-2-(6-fluoro-2,3-dimethylphenyl)-1-(5-oxo-4,5-dihydro-1,3,4-oxadiazol-2-yl)propyl)-4-hydroxychroman-8-sulfonamide Isomer A and Isomer B (Step 1) Using 5-((1,2R)-1-amino-2-(6-fluoro-2,3-dimethyl phenyl) propyl)-1,3,4-oxadiazol-2(3H)-one monohydrochloride (40 mg) obtained from Reference Example D1 and 5-fluoro-4-oxochroman-8-sulfonyl chloride (60 mg) obtained from Reference Example C3, 5-fluoro-N-((1,2R)-2-(6-fluoro-2,3-dimethyl phenyl)-1-(5-oxo-4,5-dihydro-1,3,4-oxadiazol-2-yl)propyl)-4-oxochroman-8-sulfonamide (44 mg) was obtained in accordance with the method of Example 5 Step 1.

(Step 2) Sodium borohydride (13.5 mg) was added to an ethanol (2.0 mL) solution of 5-fluoro-N-8-sulfonamide (44 mg) obtained from the above Step 1 and the reaction solution was stirred at room temperature for 30 minutes. After concentrating the reaction solution under reduced pressure, water (10 mL) and ethyl acetate (10 mL) were added to the residue, separated, and the aqueous layer was extracted with ethyl acetate (10 mL). The combined organic layer was washed with brine (10 mL), dried over anhydrous sodium sulfate, and concentrated under reduced pressure. The residue was purified by reverse phase HPLC (water/acetonitrile), and the fractions were concentrated to obtain each of two diastereomeric products. The substance eluted first was designated as Compound A, and the substance eluted later was designated as Compound B.

Example 10

According to the method of Example 5 Step 1 and Example 9 Step 2, the compounds of Example 10 shown below were synthesized. In the case of separating the diastereomers, the first eluted compound was designated as A and the later eluted compound as B. The ratio of diastereomers is 1:1 mixture unless otherwise specified. The necessary raw materials are listed in the following table.

TABLE 9

| Example | Starting Material | ArSO₂Cl | Name of the Synthesized Compound |
|---|---|---|---|
| 10A and 10B | Reference Example D1 | Reference Example C4 | 5-chloro-N-((1S,2R)-2-(6-fluoro-2,3-dimethylphenyl)-1-(5-oxo-4,5-dihydro-1,3,4-oxadiazol-2-yl)propyl)-4-hydroxychroman-8-sulfonamide |

As Comparative Example, a compound of the following formula was obtained.

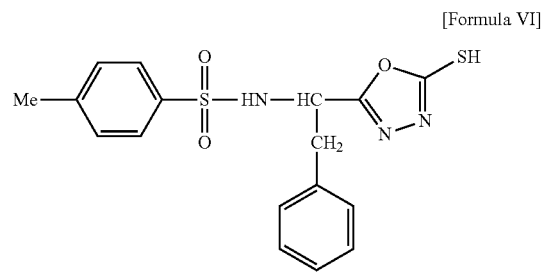 [SMILES: Cc1ccc(S(=O)(=O)NC(Cc2ccccc2)c2nnc(S)o2)cc1]

[Formula VI]

$^1$H NMR (CD3OD) δ: 7.54 (d, J=8.4 Hz, 2H), 7.17-7.29 (m, 5H), 7.08-7.14 (m, 2H), 4.55-4.61 (m, 1H), 3.00-3.13 (m, 2H), 2.39 (s, 3H)

Hereinafter, the structural formulae and physical properties of the compounds from Examples 1 to 10 are shown.

TABLE 10

| Example | Structural Formula | Physical Property Value |
|---|---|---|
| 1 |  | 1H NMR (CD3OD) δ: 7.74-7.78 (m, 3H), 6.97 (dd, J = 8.2, 5.7 Hz, 1H), 6.71 (dd, J = 11.7, 8.4 Hz, 1H), 4.78-4.81 (m, 1H), 3.51-3.61 (m, 1H), 2.20 (s, 3H), 2.17 (s, 3H), 1.44 (d, J = 7.0 Hz, 3H); LC/MS RT 1.67 min, m/z [M − H]⁻ 525, 527 |
| 2 |  | 1H NMR (CD3OD) δ: 7.84 (d, J = 8.4 Hz, 1H), 7.62 (d, J = 2.2 Hz, 1H), 7.58 (dd, J = 8.4, 2.2 Hz, 1H), 6.98 (dd, J = 8.2, 5.7 Hz, 1H), 6.72 (dd, J = 11.7, 8.4 Hz, 1H), 4.82 (d, J = 11.4 Hz, 1H), 3.50-3.60 (m, 1H), 2.20 (s, 3H), 2.17 (s, 3H), 1.45 (d, J = 7.0 Hz, 3H); LC/MS RT 1.65 min, m/z [M − H]⁻ 481, 483 |

TABLE 10-continued

| Example | Structural Formula | Physical Property Value |
|---|---|---|
| 3 | | 1H NMR (CD3OD) δ: 7.84 (d, J = 8.4 Hz, 1H), 7.62 (d, J = 2.2 Hz, 1H), 7.58 (dd, J = 8.4, 2.2 Hz, 1H), 6.98 (dd, J = 8.4, 5.9 Hz, 1H), 6.75 (dd, J = 11.7, 8.8 Hz, 1H), 4.78 (d, J = 11.0 Hz, 1H), 3.50-3.60 (m, 1H), 2.52-2.59 (m, 2H), 2.24 (s, 3H), 1.46 (d, J = 7.0 Hz, 3H), 1.06 (t, J = 7.5 Hz, 3H),; LC/MS RT 1.73 min, m/z [M − H]⁻ 495, 497 |
| 4 | | 1H NMR (CD3OD) δ: 7.86 (d, J = 8.4 Hz, 1H), 7.63 (d, J = 1.8 Hz, 1H), 7.59 (dd, J = 8.4, 2.2 Hz, 1H), 7.25 (dd, J = 8.8, 5.1 Hz, 1H), 6.88 (t, J = 10.0 Hz, 1H), 4.80 (d, J = 11.4 Hz, 1H), 3.55-3.65 (m, 1H), 2.37 (s, 3H), 1.47 (d, J = 7.0 Hz, 3H); LC/MS RT 1.68 min, m/z [M − H]⁻ 501, 503 |
| 5A | | 1H NMR (CD3OD) δ: 7.61 (d, J = 8.4 Hz, 1H), 7.02 (d, J = 8.5 Hz, 1H), 6.96 (dd, J = 8.2, 5.7 Hz, 1H), 6.70 (dd, J = 11.7, 8.4 Hz, 1H), 4.71 (d, J = 11.4 Hz, 1H), 4.40-4.46 (m, 1H), 4.26 (td, J = 10.8, 2.6 Hz, 1H), 3.62-3.71 (m, 1H), 2.23 (s, 3H), 2.17 (s, 3H), 2.05-2.13 (m, 2H), 1.50 (d, J = 7.0 Hz, 3H); LC/MS RT 1.64 min, m/z [M − H]⁻ 527, 529 |
| 5B | | 1H NMR (CD3OD) δ: 7.59 (d, J = 8.8 Hz, 1H), 7.02 (d, J = 8.4 Hz, 1H), 6.97 (dd, J = 8.4, 5.9 Hz, 1H), 6.71 (dd, J = 11.7, 8.4 Hz, 1H), 4.75 (d, J = 11.4 Hz, 1H), 4.41-4.48 (m, 1H), 4.32 (td, J = 10.7, 2.7 Hz, 1H), 3.63-3.73 (m, 1H), 2.22 (s, 3H), 2.18 (s, 3H), 2.05-2.13 (m, 2H), 1.48 (d, J = 7.0 Hz, 3H); LC/MS RT 1.71 min, m/z [M − H]⁻ 527, 529 |
| 6A | | 1H-NMR (CDCl3) δ: 8.15 (1H, s), 7.66 (1H, d, J = 8.4 Hz), 7.19 (1H, dd, J = 8.6, 5.1 Hz), 6.99 (1H, d, J = 8.6 Hz), 6.78 (1H, dd, J = 10.8, 9.0 Hz), 5.52 (1H, d, J = 11.0 Hz), 4.87 (1H, t, J = 10.4 Hz), 4.47-4.44 (1H, m), 4.28-4.25 (1H, m), 3.48 (1H, s), 3.29 (1H, s), 2.37 (3H, s), 2.32-2.28 (1H, m), 2.09-2.06 (1H, m), 1.78 (3H, s), 1.54 (3H, d, J = 7.0 Hz).; LC/MS RT 1.68 min, m/z [M − H]⁻ 544, 546 |

TABLE 10-continued

| Example | Structural Formula | Physical Property Value |
|---|---|---|
| 6B | | 1H-NMR (CDCl3) δ: 8.68 (1H, br s), 7.64 (1H, d, J = 8.8 Hz), 7.19 (1H, dd, J = 8.8, 4.9 Hz), 7.01 (1H, d, J = 8.8 Hz), 6.78 (1H, dd, J = 10.8, 8.8 Hz), 5.47-5.42 (1H, m), 4.81 (1H, t, J = 10.9 Hz), 4.45-4.42 (1H, m), 4.32 (1H, t, J = 10.9 Hz), 3.53 (1H, br s), 3.40 (1H, br s), 2.35 (3H, s), 2.33-2.27 (1H, m), 2.15-2.10 (1H, m), 1.78 (3H, s), 1.59-1.58 (3H, m).; LC/MS RT 1.74 min, m/z [M − H]⁻ 544, 546 |
| 7A | | 1H NMR (CD3OD) δ: 7.61 (d, J = 8.4 Hz, 1H), 7.42 (dd, J = 9.0, 5.3 Hz, 1H), 7.03 (d, J = 8.4 Hz, 1H), 6.81 (dd, J = 11.2, 9.0 Hz, 1H), 4.69 (d, J = 11.4 Hz, 1H), 4.39-4.47 (m, 1H), 4.22-4.33 (m, 1H), 3.63-3.78 (m, 1H), 2.44 (s, 3H), 2.17-2.24 (m, 1H), 2.05-2.15 (m, 1H), 1.75 (s, 3H), 1.52 (d, J = 6.6 Hz, 3H); LC/MS RT 1.70 min, m/z [M − H]⁻ 588, 590 |
| 7B | | 1H NMR (CD3OD) δ: 7.60 (d, J = 8.6 Hz, 1H), 7.43 (dd, J = 8.9, 5.1 Hz, 1H), 7.02 (d, J = 8.6 Hz, 1H), 6.82 (dd, J = 11.2, 8.9 Hz, 1H), 4.74 (d, J = 11.4 Hz, 1H), 4.39-4.47 (m, 1H), 4.33 (td, J = 10.8, 2.6 Hz, 1H), 3.65-3.77 (m, 1H), 2.44 (s, 3H), 2.22-2.31 (m, 1H), 2.05-2.12 (m, 1H), 1.75 (s, 3H), 1.50 (d, J = 7.0 Hz, 3H); LC/MS RT 1.76 min, m/z [M − H]⁻ 588, 590 |
| 8A | | 1H NMR (CD3OD) δ: 7.61 (d, J = 8.4 Hz, 1H), 7.24 (dd, J = 8.8, 5.1 Hz, 1H), 7.03 (d, J = 8.8 Hz, 1H), 6.87 (dd, J = 11.0, 8.8 Hz, 1H), 4.69 (d, J = 11.4 Hz, 1H), 4.41-4.47 (m, 1H), 4.26 (td, J = 10.9, 2.4 Hz, 1H), 3.65-3.72 (m, 1H), 2.39 (s, 3H), 2.15-2.25 (m, 1H), 2.05-2.13 (m, 1H), 1.52 (d, J = 6.6 Hz, 3H); LC/MS RT 1.68 min, m/z [M − H]⁻ 547, 549 |
| 8B | | 1H NMR (CD3OD) δ: 7.60 (d, J = 8.4 Hz, 1H), 7.24 (dd, J = 9.0, 4.9 Hz, 1H), 7.02 (d, J = 8.4 Hz, 1H), 6.87 (dd, J = 11.2, 9.0 Hz, 1H), 4.74 (d, J = 11.4 Hz, 1H), 4.41-4.46 (m, 1H), 4.29-4.36 (m, 1H), 3.64-3.74 (m, 1H), 2.38 (s, 3H), 2.22-2.29 (m, 1H), 2.05-2.13 (m, 1H), 1.50 (d, J = 7.0 Hz, 3H); LC/MS RT 1.74 min, m/z [M − H]⁻ 547, 549 |

TABLE 10-continued

| Example | Structural Formula | Physical Property Value |
|---|---|---|
| 9A | | 1H NMR (CD3OD) δ: 7.73 (dd, J = 8.8, 6.2 Hz, 1H), 6.96 (dd, J = 8.4, 5.9 Hz, 1H), 6.66-6.77 (m, 2H), 4.69 (d, J = 11.4 Hz, 1H), 4.84-4.90 (m, 1H), 4.53-4.60 (m, 1H), 4.35 (ddd, J = 13.1, 10.9, 2.4 Hz, 1H), 3.62-3.71 (m, 1H), 2.21 (s, 3H), 2.17 (s, 3H), 1.95-2.12 (m, 2H), 1.49 (d, J = 7.0 Hz, 3H); LC/MS RT 1.57 min, m/z [M − H]⁻ 494 |
| 9B | | 1H NMR (CD3OD) δ: 7.77 (dd, J = 8.8, 6.2 Hz, 1H), 6.97 (dd, J = 8.2, 5.7 Hz, 1H), 6.68-6.78 (m, 2H), 4.85-4.93 (m, 1H), 4.74 (d, J = 11.4 Hz, 1H), 4.51-4.60 (m, 1H), 4.33 (td, J = 11.5, 3.3 Hz, 1H), 3.62-3.71 (m, 1H), 2.22 (s, 3H), 2.18 (s, 3H), 1.96-2.09 (m, 2H), 1.47 (d, J = 6.6 Hz, 3H); LC/MS RT 1.61 min, m/z [M − H]⁻ 494 |
| 10A | | 1H NMR (CD3OD) δ: 7.66 (d, J = 8.4 Hz, 1H), 7.05 (d, J = 8.4 Hz, 1H), 6.96 (dd, J = 8.1, 5.5 Hz, 1H), 6.69 (dd, J = 11.7, 8.4 Hz, 1H), 4.86-4.93 (m, 1H), 4.71 (d, J = 11.4 Hz, 1H), 4.53-4.61 (m, 1H), 4.29-4.39 (m, 1H), 3.63-3.71 (m, 1H), 2.21 (s, 3H), 2.17 (s, 3H), 2.01-2.06 (m, 2H), 1.49 (d, J = 7.0 Hz, 3H); LC/MS RT 1.61 min, m/z [M − H]⁻ 510, 512 |
| 10B | | 1H NMR (CD3OD) δ: 7.70 (d, J = 8.4 Hz, 1H), 7.07 (d, J = 8.4 Hz, 1H), 6.97 (dd, J = 8.3, 5.7 Hz, 1H), 6.71 (dd, J = 11.7, 8.3 Hz, 1H), 4.92-4.95 (m, 1H), 4.75 (d, J = 11.4 Hz, 1H), 4.53-4.60 (m, 1H), 4.26-4.39 (m, 1H), 3.58-3.75 (m, 1H), 2.22 (s, 3H), 2.18 (s, 3H), 1.95-2.14 (m, 2H), 1.47 (d, J = 7.0 Hz, 3H); LC/MS RT 1.67 min, m/z [M − H]⁻ 510, 512 |

EXPERIMENTAL EXAMPLE

The compound according to the present disclosure was evaluated using the following test method.

Experimental Example 1: Human RNR Inhibition Effect

The inhibitory activity against the ribonucleotide reduction reaction (hereinafter referred to as RNR reaction) of the test compound was determined by measuring the formation of deoxycytidine diphosphate (hereinafter referred to as dCDP) from cytidine diphosphate (hereinafter referred to as CDP) by the following method.

Human M1 subunit and human M2 subunit (mutant lacking amino terminal 59 amino acids), which are fused a histidine tag at the amino terminus, are overexpressed in *Escherichia coli* and are solubilized after collection, and histidine tagged human M1 and M2 proteins were purified on a nickel chelate column.

For measuring the inhibitory activity of the test compound against the RNR reaction, the method described in Cancer Research 64, 1-6 (2004) was referred to.

First, test compounds were serially diluted with DMSO. Next, human M1 protein and human M2 protein were added to an aqueous albumin solution derived from 0.02% fetal bovine serum, DMSO solution of the compound of the present disclosure or the control DMSO solution (final concentration of DMSO was 1%) was added, and the mixture was allowed to stand for 20 minutes. Thereafter, the reaction buffer [50 mM HEPES buffer (pH 7.2) at the final concentration, 4 mM magnesium acetate at the final concentration, 100 mM potassium chloride at the final concentration, 6 mM dithiothreitol at the final concentration, 2 mM adenosine triphosphate at the final concentration, 0.24 mM nicotinamide adenine dinucleotide phosphate at final concentration] and 10 µM CDP at the final concentration were added and incubated at 37° C. for 30 minutes to perform RNR reaction. Immediately after the reaction, the reaction was stopped by heating at 100° C. for 15 minutes, followed by centrifugation at 10,000 rpm for 10 minutes. After the centrifugation, a portion (5 µL) of the resulting supernatant was analyzed with a high performance liquid chromatography (Shimadzu Corporation, Prominence) using Shim-pack XR-ODS (manufactured by Shimadzu GLC Co., 3.0×100 mm). Elution was carried out at a measurement wavelength of 265 nm at a flow rate of 0.5 mL/min by a 9-minute concentration gradient from the 12:13 mixture of mobile phase A (10 mM potassium dihydrogen phosphate (pH 6.7), 10 mM tetrabutylammonium, 0.25% methanol) and mobile phase B (50 mM potassium dihydrogen phosphate (pH 6.7), 5.6 mM tetrabutylammonium, 30% methanol) to the same 2:3 mixture to measure the substrate CDP (RT 5.9 min) and the reaction product dCDP (RT 6.2 min).

The inhibitory activity of the test compound was determined by the following equation, and the concentrations of test compounds inhibiting the RNR reaction by 50% are shown as $IC_{50}$ (µM) in Tables 19-1 to 19-3.

[Mathematical Formula 1]

$$\text{Inhibition rate (\%)} = \left(1 - \frac{\text{Amount of produced } dCDP \text{ where test compound added (pmol)}}{\text{Amount of produced } dCDP \text{ of control (pmol)}}\right) \times 100$$

As a result, it is apparent from the following table that the compound of the present invention has an excellent RNR inhibitory action. In contrast, the compound of Comparative Example 1 had an $IC_{50}$ of 43 µM, and showed no inhibitory activity against RNR as found in the example compounds of the present invention.

TABLE 11

| Example | RNR Enzyme inhibitory activity $IC_{50}$ (µM) |
|---|---|
| 1 | 0.06 |
| 2 | 0.14 |
| 3 | 0.18 |
| 4 | 0.25 |
| 5A | 0.03 |
| 5B | 0.08 |
| 6A | 0.10 |
| 6B | 0.18 |
| 7A | 0.08 |
| 7B | 0.06 |
| 8A | 0.08 |
| 8B | 0.14 |

TABLE 11-continued

| Example | RNR Enzyme inhibitory activity $IC_{50}$ (µM) |
|---|---|
| 9A | 0.12 |
| 9B | 0.05 |
| 10A | 0.08 |
| 10B | 0.07 |

Experimental Example 2: Cell Proliferation Inhibitory Effect on Human Breast Cancer Cell Line Human derived breast cancer cell line HCC 1806 cells were daily passaged at a cell density not exceeding 80% in ATCC recommended Roswell Park Memorial Institute medium (RPMI-1640) containing 10% fetal bovine serum (FBS). In order to start the test of cell proliferation inhibitory activity, HCC 1806 cells were suspended in the above medium, after seeing at 180 µL in each well of a 96-well flat bottom plate so that the number of cells per well was 2,000, the cells were cultured at 37° C. for 1 day in an incubator containing 5% carbon dioxide gas. On the next day, the test compound was dissolved in DMSO, and 20 µL of a drug additive solution diluted serially with distilled water to 10 times of the final concentration was added to each well of the culture plate of the cells, and the cells were cultured at 37° C. for 72 hours in an incubator containing 5% carbon dioxide gas. After culturing for 72 hours, 20 µL of glutaraldehyde was added to each well and allowed to stand for 30 minutes, then the plate was washed 10 times with water and was dried. 100 µL of a stain solution (0.05% crystal violet in a 20% methanol solution) was added to each well and allowed to stand for 30 minutes, then the plate was washed 10 times with water and was dried. 100 µL of an extract solution (0.1 N $NaH_2PO_4$: 100% ethanol=1:1) was added to each well and mixed, and the mixture was measured at a wavelength of 540 nm using a plate reader (MTP-450 manufactured by Corona Electric Co., Ltd.). The growth inhibition rate was calculated from the following formula, and the concentration ($IC_{50}$ (µM)) of a test compound inhibiting 50% was determined. The results are shown in Table 11.

Growth inhibition rate (%)={(C−B)−(T−B)}/(C−B)×100

T: Absorbance of well to which test compound was added
C: Absorbance of wells to which no test compound was added
B: Absorbance of wells to which no cell suspension was added As a result, as is clear from the following table, it was revealed that the compounds of the present disclosure have growth inhibitory activity against cancer cells.

TABLE 12

| Example Number | Cell growth suppression $IC_{50}$ (µM) |
|---|---|
| 1 | 0.16 |
| 2 | 0.20 |

TABLE 12-continued

| Example Number | Cell growth suppression IC$_{50}$ (μM) |
|---|---|
| 3 | 0.64 |
| 4 | 0.56 |
| 5A | 0.05 |
| 5B | 0.46 |
| 6A | 0.06 |
| 6B | 0.82 |
| 7A | 0.06 |
| 7B | 0.67 |
| 8A | 0.14 |
| 9A | 0.29 |
| 9B | 0.78 |
| 10A | 0.13 |
| 10B | 0.40 |

Experimental Example 3 Cell Proliferation Inhibitory Effect on Human Cancer-Derived Cancer Cell Lines According to the method of Experimental Example 2, the cell proliferation inhibitory effect on various cancer cell lines as described in Tables 12 and 13 was evaluated.

As a result, as is clear from the following table, it was revealed that the compounds of the present disclosure have growth inhibitory activity against various types of cancer cells derived from humans.

TABLE 13

| cell line | NUGC-3 | NCI-H460 | CFPAC-1 | A673 | GB-1 | HLE | MSTO-211H | DU145 |
|---|---|---|---|---|---|---|---|---|
| Carcinoma type | Stomach Cancer | Lung Cancer | Pancreatic Cancer | Ewing's sarcoma | Glioblastoma | Liver Cancer | Mesothelioma | Prostate Cancer |
| Culture medium | RPMI-1640 +10% FBS | ATCC recommended RPMI-1640 +10% FBS | IMDM +10% FBS | DMEM +10% FBS | DMEM +10% FBS | DMEM +10% FBS | ATCC recommended RPMI-1640 +10% FBS | EMEM +0.1 mM non-essential amino acid +1 mM sodium pyruvate +10% FBS |
| cell number (cell/well) | 2000 | 1000 | 2000 | 2000 | 3000 | 3000 | 6000 | 5000 |
| Example 2 | 1.22 | 0.73 | 0.94 | 1.09 | 1.57 | 0.79 | 0.70 | 1.04 |
| Example 10A | 0.71 | 0.35 | 0.35 | 0.61 | 1.12 | 0.42 | 0.39 | 0.53 |
| Example 3 | 3.11 | 1.50 | 1.71 | 2.56 | 5.22 | 1.74 | 1.54 | 1.84 |
| Example 1 | 1.12 | 0.57 | 0.54 | 0.92 | 1.56 | 0.56 | 0.65 | 0.73 |
| Example 6A | 0.40 | 0.25 | 0.33 | 0.32 | 0.64 | 0.26 | 0.32 | 0.31 |
| Example 7A | 0.36 | 0.18 | 0.23 | 0.25 | 0.46 | 0.20 | 0.27 | 0.26 |
| Example 5A | 0.27 | 0.13 | 0.17 | 0.18 | 0.37 | 0.14 | 0.17 | 0.17 |
| Example 8A | 0.51 | 0.31 | 0.36 | 0.40 | 0.85 | 0.29 | 0.37 | 0.34 |

TABLE 14

| cell line | A2780 | ACHN | HCT116 | RPMI7932 | NCI-H2228 | NCI-H2170 |
|---|---|---|---|---|---|---|
| Carcinoma type | Ovarian Cancer | Kidney Cancer | Colorectal Cancer | Melanoma | Lung Cancer | Lung Cancer |
| Culture medium | RPMI-1640 +10% FBS | EMEM +10% FBS | McCoy's 5A +10% FBS | RPMI-1640 +10% FBS | ATCC recommended RPM1-1640 +10% FBS | ATCC recommended RPM1-1640 +10% FBS |
| cell number (cell/well) | 2000 | 2000 | 1000 | 4000 | 5000 | 5000 |
| Example 2 | 0.83 | 0.75 | 0.91 | 2.67 | 1.27 | 1.89 |
| Example 10A | 0.40 | 0.38 | 0.48 | 1.23 | 0.88 | 1.10 |
| Example 3 | 2.08 | 1.50 | 2.30 | 4.74 | 3.21 | 3.90 |
| Example 1 | 0.63 | 0.68 | 0.75 | 1.74 | 1.35 | 1.41 |
| Example 6A | 0.30 | 0.22 | 0.28 | 0.72 | 0.73 | 0.57 |
| Example 7A | 0.19 | 0.17 | 0.27 | 0.51 | 0.48 | 0.52 |
| Example 5A | 0.13 | 0.13 | 0.22 | 0.43 | 0.50 | 0.49 |
| Example 8A | 0.38 | 0.32 | 0.38 | 0.65 | 0.74 | 0.88 |

Experimental Example 4: Evaluation of Antitumor Effect Using Human-Derived Blood Cancer Cell Line (MV-4-11) Subcutaneous Transplantation Model (In Vivo)

A human-derived blood cancer cell line MV-4-11 was transplanted subcutaneously into a nude mouse, and at the time when the tumor volume of the nude mouse on which the engrafted tumor reached about 100 to 300 mm$^3$, four mice were assigned to each group by random stratification so that the average of the tumor volumes of each group was uniform (day 0), and the compound of the present disclosure was orally administered daily at 100 mg/kg/day once per day for 14 days.

In order to compare the chronological transition of proliferation of tumor for the administration of each test compound, relative tumor volume (RTV) setting the tumor volume at the time of grouping as 1 as the tumor proliferation rate was calculated according to the following formula, and the transition of the average value of RTV of each individual are shown in FIGS. 1 to 4.

RTV=(tumor volume at the day of tumor volume measurement)/(tumor volume at the time of the grouping)

The average RTV value of the compound-administered group of the present disclosure on the final evaluation day is smaller than the average RTV value of the control group, and when a statistically significant difference (Student-t test) is shown, the compound of the present disclosure was determined to be significantly effective, and the statically significant difference is marked with * in the figure (*: $p<0.05$).

As a result, it was revealed that the compound of the present disclosure shows a significant antitumor effect.

Experimental Example 5: Forming of Crystalline Form, Co-Crystal, or Salt Exemplary Sample A compound selected from Examples 1-10 above was tried to be crystallized with a total of 47 secondary compounds (Sodium hydroxide, Potassium hydroxide, L-Arginine, Calcium Hydroxide, Choline hydroxide, Diethylamine, L-Lysine, Diethanolamine, Tromethamine, Ethylenediamine, Oxalic acid, Dibenzoyl-L-tartaric acid, Maleic acid, Glutamic acid, Malonic acid, Fumaric acid, L-Tartaric acid, 4-hydroxybenzamide, Nicotinamide, Isonicotinamide, Saccharine, Galactaric acid, Citric acid, D-Glucoronic acid, L-Malic acid, Ethylenediamine, Glutaric acid, Succinic acid, Urea, Arginine, Benzoic acid, ascorbic acid, methylparaben, vanillin, glycolic acid, hydrochloric acid, hippuric acid, L-lactic acid, methane-sulfonic acid, phosphoric acid, p-toluene-sulfonic acid monohydrate, sulfuric acid, L-alanine, glycine, meglumine, L-proline, L-serine, L-valine), but only the combination with benzoic acid formed a crystalline form, co-crystal or salt exemplary sample.

Initially, 93 mg of the compound selected from Examples 1-10 was dissolved in 500 µL of isopropyl acetate and the solution was stirred at 60° C.; 233 µL of a benzoic acid solution in methanol (concentration: 0.8672 mmol/mL) was added into the sample. The mixture was stirred at 60° C. for 10 minutes, filtered through a pre-warmed syringe filter (0.2 µm, nylon), and then cooled to the ambient temperature, followed by sub-ambient storage, evaporation and stirring the gel resulted from the evaporation in 1 mL heptane at ambient conditions for 30 days to obtain the exemplary sample containing 1 equivalent of benzoic acid. However, in this production method, it took more than 30 days manufacturing period and only about 10 mg of the exemplary sample was obtained.

In another example, 3 g of an exemplary sample was obtained by a method of suspending the similar amount of the same compound in a heptane-toluene mixed solvent and stirred at 40° C. or higher. For example, to 3000 mg of the compound selected from Examples 1-10, 1518 mg of benzoic acid was added, and 57 mL of heptane and 3 mL of toluene were added thereto. The suspension was stirred for about 4.5 hours under heating at 60° C. The suspension was collected by filtration, washed with a 19:1 mixture of heptane and toluene and was heated at 60° C. The solid was recovered and dried to obtain 3420.6 mg (recovery rate 91%) of the product with 98.67% chemical purity and 100% ee optical purity. H-NMR (CDCl$_3$) δ: 8.77 (s, 1H), 8.09 (d, J=8.0 Hz, 2H), 7.89 (d, J=8.0 Hz, 1H), 7.60 (t, J=7.2 Hz, 1H), 7.54 (d, J=2 Hz, 1H), 7.40-7.51 (m, 3H), 6.91 (dd, J=6.0 Hz, 8.4 Hz, 1H), 6.87 (d, 9.6 Hz, 1H), 6.67 (dd, J=8.0 Hz, 8.4 Hz, 1H), 6.55 (br s, 1H), 6.34 (br s, 1H), 4.88 (dd, J=9.6 Hz, 10.4 Hz, 1H), 3.40-3.55 (m, 1H), 2.15 (s, 6H), 1.42 (d, J=6.8 Hz, 3H).

The suspension was filtered, and the solid was rinsed with the mixture of heptane and toluene and heated at 60° C. As a result of evaluating the physicochemical properties of the obtained crystalline form, co-crystal or salt, it was surprisingly found that this product is excellent in storage stability, further has low hygroscopicity and chargeability, and is easy to handle.

In another example, to 1000 mg of the compound selected from Examples 1-10, 506 mg of benzoic acid was added, and 19 mL of heptane and 1 mL of toluene were added thereto. The suspension was stirred for about 3.5 hours under heating at 60° C. The suspension was collected by filtration, washed with a 19:1 mixture of heptane and toluene, and was heated at 60° C. The solid was recovered and dried to obtain 947 mg (recovery rate: 75.6%) of an exemplary sample.

In addition, among 47 kinds of secondary compounds used for crystallization study, there were secondary compounds containing a basic functional group (or cation), but the present compound, which is acidic, did not form a crystal with these basic secondary compounds. Thus, it was unexpected that the acidic compound formed a crystalline form, co-crystal or salt only with benzoic acid, which is an acidic compound. Furthermore, it is unforeseeable what kind of physicochemical properties the obtained crystalline form, co-crystal or salt has.

Experimental Example 6: Structural Characteristics

Single crystal analysis: 5 mL of heptane, 3 mL of n-propyl acetate, and 203.3 mg of benzoic acid were added to 100 mg of the sample from Experimental Example 5 using the compound of Example 2 (hereinafter also referred to as "the exemplary sample of the present invention"), and dissolved at 80° C. To the dissolved product, 810 mg of benzoic acid was added and dissolved. A small amount of the product was added, and the mixture was allowed to stand overnight at 60° C. Thereafter, the temperature was lowered to 50° C. and allowed to stand for 6 days to obtain crystals for single crystal analysis.

Measurement was performed under the following measurement conditions, and data processing was carried out using data measurement and processing software CrysAlis-Pro, structure analysis program package CrystalStructure, and integrated powder X-ray analysis software PDXL.

Apparatus: XtaLAB PRO MM 007
X-ray source: Cu Kα (λ=1.54184 Å)
Tube voltage•tube current: 40 kV-30 mA
Measurement temperature: −173° C. (using spraying low temperature device)
Collimator diameter: ϕ0.3 mm
Camera length: 39.71 mm
Vibration angle: 0.25°
Exposure time: 0.25 sec/piece
Total number of measurements: 14476 sheets
Total measurement time: 1 hour 35 minutes
The results are shown below and in FIG. 5.
Crystal system: monoclinic system
Space group: P21/n (No. 4)
Lattice constant: a=13.89023 (9) Å
b=7.77623 (4) Å
c=14.00408 (9) Å
α=90°
β=110.5202 (7) °
γ=90°
Volume of unit cell: 1416.653 (16) Å 3

The powder X-ray diffraction data of the exemplary sample of the present invention was measured according to the following test conditions.

Apparatus: EMPYREAN made by PANalytical
Reflection method (intensive method)
Target: Cu
X-ray tube current: 40 mA
X-ray tube voltage: 45 kV
Scanning range: 2θ=5.0 to 40.0°
Step: 2θ=0.0131°
Average time/step: 8.670s
Scan speed: 0.0015°/s
Divergence slit: 1°
Scattering slit: 2.0 mm
Receiving slit: 8.0 mm X-ray diffraction spectrum is shown in FIG. 6. The powder X-ray diffraction pattern of the sample has a diffraction angle (2θ±0.2°) of 6.8°, 7.8°, 11.2°, 13.4°, 13.7°, 16.0°, 17.1°, 17.8° and 23.2°.

Experimental Example 7: Differential Scanning Calorimetry (DSC Measurement)

DSC measurement of exemplary sample of the present invention was performed according to the following test conditions.

Apparatus: DSC 1 STAR System made by METTLER TOLEDO
Sample: Approximately 1 mg
Sample container: made of aluminum
Raising range: 25 to 290° C.
Rate of temperature increase: 10° C./min.
Atmospheric gas: nitrogen
Nitrogen gas flow rate: 50 mL/min.

Handling of devices including data processing was in accordance with the manual provided with the DSC device. The resulting DSC curve is shown in FIG. 7. As shown in the DSC result, an endothermic peak (peak top) was shown at 162° C.

FIG. 9 shows the result of simulating the XRD diffraction pattern from the result of the single crystal analysis, and the characteristic peaks of the diffraction angle (2θ±0.2°) (6.8°, 7.8°, 11.2°, 13.4°, 13.7°, 16.0°, 17.1°, 17.8° and 23.2°) matches with the example above.

Experimental Example 8: Hygroscopicity

The moisture adsorption/desorption test was carried out according to the following conditions.

Approximately 10 to 15 mg of the sample was filled in a dedicated quartz holder, and the weight of each sample at each humidity was continuously measured and recorded under the following conditions. The handling of the device including data processing was in accordance with the method and procedure instructed by each device.

Apparatus: VTI SA+(manufactured by TA Instruments Inc.)
Drying temperature: 60° C.
Heating rate: 1° C./min
Drying equilibrium: In the range not exceeding 300 minutes, confirm that it does not decrease by 0.01 wt % in 5 minutes
Measurement temperature: 25° C.
Humidification equilibrium: In the range not exceeding 120 minutes, confirm that it does not increase by 0.01 wt % in 5 minutes
Relative Humidity Program: Increase by 5% RH to 5 to 95% RH and lower by 5% RH from 95% RH to 5% RH When a free form of the compound was initially obtained as an amorphous substance, the free form had hygroscopicity (FIG. 8) and also had high charging property. Here, "free form" refers to an amorphous substance by the drug substance alone. As described above, however, crystalline form, co-crystal or salt of the free form of the compound of Example 2 was obtained, and this sample had no hygroscopicity (FIG. 8) and weak charging property.

As shown in FIG. 8, the hygroscopicity of the obtained product (pulverized product) was a mass change of about 0.1% under a relative humidity of 95% in the moisture adsorption/desorption test, and thus the product exhibited almost no hygroscopicity. These physicochemical properties are superior to the hygroscopicity and chargeability of the free form of the same compound.

The obtained solid product of Example 2 had low charging property and a small amount of adhesion to a spatula or a glass bottle was observed.

As a Comparative Example, the compound above, spray drying was carried out in order to remove residual solvent. 2 g of the compound was dissolved in 18 g of ethanol, and spray drying was carried out under the following conditions.

After heat input warming: progression
Exhaust heat temperature 78° C.
Feed flow rate 5 mL/min
Spray nitrogen flow rate 350 L/hour The obtained spray-dried product was dried under reduced pressure in an atmosphere at 90° C. for 1 hour to obtain a free form of the compound, which was amorphous, had a high charging property, and exhibited much adhesion when it was transferred by a spatula or a glass bottle. Further, as shown in FIG. 8, a mass increase of about 3.8% was observed under 95% relative humidity in the moisture adsorption/desorption test. This Comparative Example was also used for the stability test below.

Experimental Example 9: Stability Test

Initially, the chemical purity was measured by the following methods.

The amount of analogous substances in the sample solution was measured by HPLC analysis. The handling of the device including data processing was in accordance with the manual provided with the device. (i.e., Prominence-i). About 2 mg of the exemplary sample of the present invention was dissolve in 4 mL of mobile phase A/mobile phase B mixture (17: 3), and the resulting mixture was used as sample solution.

Column: CAPCELL PAK ADME manufactured by Shiseido (4.6×150 mm, 3 μm)
UV detection: 220 nm
Column temperature: 40° C.
Column flow rate: 1.0 mL/min
Mobile phase: A; 5 mM phosphate buffer, pH 6.2/Acetonitrile (4:1)
B: acetonitrile
Injection volume: 5 μL
Sample cooler temperature: 5° C.
Collection time: 40 minutes

TABLE 15

Gradient for HPLC

| Time (min) | Mobile Phase A vol % | Mobile Phase B vol % |
|---|---|---|
| 0-10 | 85→68 | 15→32 |
| 10-22 | 68 | 32 |
| 22-32 | 68→35 | 32→65 |
| 32-40 | 35 | 65 |
| 40-41 | 35→85 | 65→15 |
| 41-50 | 85 | 15 |

The solid stability of the exemplary sample of the present invention and the free form obtained above was tested after the sample was stored at 40° C./75% RH (closed and open condition) for 2 weeks or 4 weeks. Open condition means that the lid of the glass bottle was removed and covered with Kimwipe.

Measurement points: 2 weeks and 4 weeks
Storage amount: about 50 to 60 mg
Storage container: brown glass bottle

TABLE 16

|  | Initial | 40° C./75% RH (Open) | | 40° C./75% RH (Closed) | |
|---|---|---|---|---|---|
|  |  | 2 wks | 4 wks | 2 wks | 4 wks |
| Comparative Example Chemical Purity (%) | 98.49 | 98.35 | 98.14 | 98.42 | 98.16 |
| Comparative Example Total amount of analogous substances (%) | 1.51 | 1.65 | 1.86 | 1.58 | 1.84 |
| Exemplary Sample Chemical Purity (%) | 98.67 | 98.67 | 98.60 | 98.67 | 98.62 |
| Exemplary Sample Total amount of analogous substances (%) | 1.33 | 1.33 | 1.40 | 1.33 | 1.38 |

After the storage, the sample produced only a small amount of analogous substances, exhibiting superior stability compared to the Comparative Example having a free form. Therefore, it was confirmed that the sample of the present disclosure exhibits excellent stability.

The optical purity was also measured by the following HPLC condition

Detector: UV at 240 nm
Column: CHIRALPAK IE (4.6×250 mm, 5 μm)/Daicel corp.
Column temperature: 40° C.
Mobile phase: n-hexane/ethanol/ethanolamine/acetic acid (65:35:0.5:0.2)
Flow rate: 1.0 mL/min
Injection: 5 μL
Sample temperature: 5° C.
Time span of measurement: 40 min
Limit of Quantitation (LOQ):
  Compound—RR,RS,SS: 0.05%

The optical purity was measured also with added 0.2% optical isomer.

The solid stability of the exemplary sample of the present invention and the free form obtained above was tested before and after the sample was stored at 40° C./75% RH (closed and open condition) for 24 hours. No significant change in the optical purity was observed after 24 hours.

The results from the optical purity measurement study are shown in FIGS. 10-12.

Experimental Example 10: Solubility Test

About 15 mg of the exemplary sample of the present invention was added to 1 mL of each solvent and was swelled at 37° C. for 2 hours under light resistant condition. After centrifugation, each supernatant was filtered, and 0.7 mL of a mixture of water and acetonitrile (1:1) was added to 0.1 mL of the filtrate. The solubility test was performed with 5 μL of the solvent according to the following conditions.

Detector: An Ultraviolet spectrophotometer (wavelength: 230 nm)
Column: CAPCELPAK ADME (4.6×150 mm, 3 mm)
Column temperature: constant temperature of about 40° C.
Mobile Phase A: A: mixture of 5 mM phosphate buffer (pH 6.52) and Acetonitrile (4:1)
B: Acetonitrile
Following of mobile phase: Control the gradient by mixing the mobile phase A and B as directed in the following table below
Flow rate: 1.0 mL per minutes
Time span of measurement: For 12 minutes after injection

TABLE 17

Gradient for HPLC

| Time after injection of sample (min) | Mobile phase A (vol %) | Mobile phase B (vol %) |
|---|---|---|
| 0-4 | 70→30 | 30→70 |
| 4-12 | 30 | 70 |
| 12-13 | 30→70 | 70→30 |
| 13-18 | 70 | 30 |

The results from the solubility test are shown in Table 18 below.

TABLE 18

Solubility data

| | Solubility (mg/mL) | |
|---|---|---|
| solvent | Free acid | Exemplary Sample |
| water | 0.23 | 0.23 |
| First fluid for dissolution test, pH 1.2 | 0.23 | 0.23 |
| Acetate buffer (50 mM, pH 4.0) | 0.25 | 0.26 |

TABLE 18-continued

Solubility data

| solvent | Solubility (mg/mL) | |
|---|---|---|
| | Free acid | Exemplary Sample |
| Second fluid for dissolution test, pH 6.8 | 0.80 | 0.61 |
| 0.5% HPMC | 0.19 | 0.13 |

No significant change was observed on XRD pattern after 2 hr solubility study, and no significant different was observed between a free acid form and the exemplary sample of the present invention.

Experimental Example 11: Solid Stability Test

The solid stability of the exemplary sample of the present invention and the free form obtained above was tested after the sample was stored at 40° C./75% RH (open condition), 70° C. (closed) and 80° C. (closed) after 2 weeks or 4 weeks. Open condition means that the lid of the glass bottle was removed and covered with Kimwipe, 70° C. and 80° C. (closed).

Measurement points: 2 weeks and 4 weeks

Storage amount: about 30 mg

Storage container: brown glass bottle

The amount of analogous substances in the sample solution was measured by HPLC analysis. The handling of the device including data processing was in accordance with the manual provided with the device. (i.e., Prominence-i). About 2 mg of the exemplary sample of the present invention was dissolve in 4 mL of mobile phase A/mobile phase B mixture (17: 3), and the resulting mixture was used as sample solution.

Column: CAPCELL PAK ADME manufactured by Shiseido (4.6×150 mm, 3 μm)

UV detection: 220 nm

Column temperature: 40° C.

Column flow rate: 1.0 mL/min

Mobile phase: A; 5 mM phosphate buffer, pH 6.5/Acetonitrile (4:1)

B: acetonitrile

Injection volume: 5 μL

Sample cooler temperature: 5° C.

Collection time: 40 minutes

TABLE 19

Gradient for HPLC

| Time (min) | Mobile Phase A vol % | Mobile Phase B vol % |
|---|---|---|
| 0-10 | 85→68 | 15→32 |
| 10-22 | 68 | 32 |
| 22-32 | 68→35 | 32→65 |
| 32-40 | 35 | 65 |
| 40-41 | 35→85 | 65→15 |
| 41-50 | 85 | 15 |

TABLE 20

| | 40° C. 75% RH (Open) | | 70° C. (Closed) | | 80° C. (Closed) | |
|---|---|---|---|---|---|---|
| | Initial | 4wks | 2 wks | 4 wks | 2 wks | 4 wks |
| Comparative Example Chemical Purity (%) | 98.33 | 97.97 | 97.31 | 96.39 | 95.90 | 92.92 |
| Comparative Example Total amount of analogous substances (%) | 1.67 | 2.03 | 2.69 | 3.61 | 4.10 | 7.08 |
| Exemplary Sample Chemical Purity (%) | 99.69 | 99.69 | 99.67 | 99.68 | 99.66 | 99.66 |
| Exemplary Sample Total amount of analogous substances (%) | 0.31 | 0.31 | 0.33 | 0.32 | 0.34 | 0.34 |

The invention claimed is:

1. A crystalline form of 5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide, wherein a powder X-ray diffraction pattern of the crystalline form has two or more peaks at (2θ±0.2°) of 6.8°, 7.8°, 11.2°, 13.4°, 13.7°, 16.0°, 17.1°, 17.8° and 23.2°.

2. A crystalline form of 5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide, wherein a powder X-ray diffraction pattern of the crystalline form has five or more peaks at (2θ±0.2°) of 6.8°, 7.8°, 11.2°, 13.4°, 13.7°, 16.0°, 17.1°, 17.8° and 23.2°.

3. A crystalline form of 5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide, wherein a powder X-ray diffraction pattern of the crystalline form has seven or more peaks at (2θ±0.2°) of 6.8°, 7.8°, 11.2°, 13.4°, 13.7°, 16.0°, 17.1°, 17.8° and 23.2°.

4. The crystalline form of claim 1, wherein a chemical purity of the crystalline form is 90% or more.

5. The crystalline form of claim 2, wherein a chemical purity of the crystalline form is 90% or more.

6. The crystalline form of claim 3, wherein a chemical purity of the crystalline form is 90% or more.

7. The crystalline form of claim 1, wherein an optical purity of the crystalline form is 100% ee.

8. The crystalline form of claim 2, wherein an optical purity of the crystalline form is 100% ee.

9. The crystalline form of claim 3, wherein an optical purity of the crystalline form is 100% ee.

10. The crystalline form of claim 1, wherein the crystalline form is stable upon exposure to about 40° C. and about 75% relative humidity for about four weeks.

11. The crystalline form of claim 2, wherein the crystalline form is stable upon exposure to about 40° C. and about 75% relative humidity for about four weeks.

12. The crystalline form of claim 3, wherein the crystalline form is stable upon exposure to about 40° C. and about 75% relative humidity for about four weeks.

13. The crystalline form of claim 1, wherein the crystalline form is a co-crystal of benzoic acid and 5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide.

14. The crystalline form according to claim 13, wherein the molar ratio of the 5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide and the benzoic acid is 1:1.

15. The crystalline form of claim 2, wherein the crystalline form is a co-crystal of benzoic acid and the 5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide.

16. The crystalline form according to claim 15, wherein the molar ratio of the 5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide and the benzoic acid is 1:1.

17. The crystalline form of claim 3, wherein the crystalline form is a co-crystal of benzoic acid and the 5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide.

18. The crystalline form according to claim 17, wherein the molar ratio of the 5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide and the benzoic acid is 1:1.

19. A pharmaceutical composition comprising the crystalline form of claim 1.

20. A pharmaceutical composition comprising the crystalline form of claim 2.

21. A pharmaceutical composition comprising the crystalline form of claim 3.

22. An anti-tumor agent comprising the crystalline form of claim 1.

23. The anti-tumor agent of claim 22, wherein the anti-tumor agent is an oral anti-tumor agent.

24. An anti-tumor agent comprising the crystalline form of claim 2.

25. The anti-tumor agent of claim 24, wherein the anti-tumor agent is an oral anti-tumor agent.

26. An anti-tumor agent comprising the crystalline form of claim 3.

27. The anti-tumor agent of claim 26, wherein the anti-tumor agent is an oral anti-tumor agent.

* * * * *